(12) United States Patent
Takayama et al.

(10) Patent No.: US 6,982,257 B1
(45) Date of Patent: Jan. 3, 2006

(54) VITAMIN $D_3$ DERIVATIVE AND ITS PRODUCTION METHOD

(75) Inventors: Hiroaki Takayama, Kanagawa (JP); Katsuhiro Konno, Kanagawa (JP); Toshie Fujishima, Kanagawa (JP)

(73) Assignee: Teijin Limited, Osaka (JP)

( * ) Notice: Subject to any disclaimer, the term of this patent is extended or adjusted under 35 U.S.C. 154(b) by 389 days.

(21) Appl. No.: 09/214,155

(22) PCT Filed: Apr. 30, 1998

(86) PCT No.: PCT/JP98/01979

§ 371 (c)(1),
(2), (4) Date: Dec. 29, 1998

(87) PCT Pub. No.: WO98/50353

PCT Pub. Date: Nov. 12, 1998

(30) Foreign Application Priority Data

May 2, 1997 (JP) ............................................. 9-114695

(51) Int. Cl.
*A61K 31/59* (2006.01)
*C07C 401/00* (2006.01)

(52) U.S. Cl. ........................................ 514/167; 552/653
(58) Field of Classification Search ................ 514/167; 552/653
See application file for complete search history.

(56) References Cited

U.S. PATENT DOCUMENTS

| 5,389,622 | A | * | 2/1995 | Posner et al. ................ 514/167 |
| 5,552,392 | A | | 9/1996 | DeLuca et al. |
| 5,585,369 | A | | 12/1996 | DeLuca et al. |
| 5,877,168 | A | * | 3/1999 | Miyamoto et al. ........... 514/167 |
| 6,124,276 | A | * | 9/2000 | Miyamoto et al. ........... 514/167 |

FOREIGN PATENT DOCUMENTS

| JP | 6-41059 | 2/1994 |
| WO | WO 95/17363 | 6/1995 |

OTHER PUBLICATIONS

S. Nayeri et al; High–Affinity Nuclear Receptor Binding of 20–epi Analogues of 1,25–Dihydroxyvitamin D3 Correlates Well with Gene Activation; Feb. 2, 1996; pp. 325–333, J. of Cellular Biochemistry 62:325–333 (1996).

G. Posner et al; 2–Fluoroalkyl A–Ring Analogs of 1,25–Dihydroxyvitamin D3. Stereocontrolled Total Synthesis Via Intramolecular and Intermolecular Diels–Alder Cycloadditions, Preliminary Biological Testing; 1995; pp. 4617–4628; vol. 60; vol. 60, No. 14, J. Org. Chemistry.

Kobayashi et al; 116th (1996) Congress of The Pharmaceutical Society of Japan, Abstract 3, 88.

Maki et al; 116th (1996) Congress of the Pharmaceutical Society of Japan, Abstract 2,9.

Katsuhiro Konno, et al.: "A Novel and Practical Route to A–Ring Enyne Synthon for 1α, 25–Dihydroxyvitamin $D_3$ Analogs: Synthesis of A–Ring Diastereomers of 1α, 25–Dihydroxyvitamin $D_3$." Bioorganic & Medicinal Chemistry Letters, vol. 8, No. 2, Jan. 20, 1998, p. 151–156. XP004136835.

* cited by examiner

*Primary Examiner*—Sabiha N. Qazi
(74) *Attorney, Agent, or Firm*—Sughrue Mion, PLLC

(57) ABSTRACT

Provided are 1,25-dihydroxy-2-methylvitamin D3 derivatives expressed by the general formula (I),

[wherein each of $R_1$ and $R_2$ is independently a hydrogen atom or a tri($C_1$ to $C_7$ alkyl)silyl group; herein configurations of asymmetric carbons at the 1-, 2- and 3-positions are each independently α-configuration or β-configuration] and their production methods.

The compound is useful as a treating agent for osteoporosis, rickets, hyperthyroidism, etc.

2 Claims, No Drawings

VITAMIN D₃ DERIVATIVE AND ITS PRODUCTION METHOD

TECHNICAL FIELD

The present invention relates to a new vitamin $D_3$ derivative having a methyl group at the 2-position and its production method. More particularly, the invention relates to 1,25-dihydroxy-2-methylvitamin D3 derivatives useful as a treating agent for osteoporosis and their production methods.

BACKGROUND ART

Hitherto, it has been well known through patent publications and general scientific literature that an active vitamin $D_3$ plays an extremely important role as a substance controlling the metabolism of calcium, phosphates, etc., in a living body. Further, it is widely known that various kinds of vitamin D derivatives have been used as treating agents for metabolic disorders of vitamin D including osteoporosis and rickets.

Furthermore, there is a report that the fact in which vitamin $D_3$ has calcium controlling activity and other various kinds of biological activities found in vitamin $D_3$ is considered attributable to the occurrence of various kinds of selectivity based on the difference between a binding affinity to a vitamin D receptor and that to a vitamin D binding protein.

As a known 2-position substituted vitamin $D_3$ derivative, 1,25-dihydroxyvitamin $D_3$ derivatives, which have a hydroxyl group of α-configuration at the 1-position and a substituent (no substituent, a $C_1$ to $C_6$ linear alkyl group substituted with a hydroxyl group at the terminal, a $C_1$ to $C_6$ linear alkyloxy group substituted with a hydroxyl group at the terminal, a $C_1$ to $C_5$ alkenyl group or a hydroxyl group) of β-configuration at the 2-position, have been reported [Kobayashi, et al., 116th (1996) Congress of The Pharmaceutical Society of Japan, Abstract 3, 88].

Further, 1,25-dihydroxyvitamin $D_3$ derivatives having a hydroxyl group of α-configuration at the 1-position and a substituent (3-hydroxypropyl group or 3-fluoropropyl group) of α-configuration at the 2-position have been reported [Posner, G. H., J. Org. Chem., 60, 4617 (1995)].

Furthermore, there is a report of a study concerning other stereoisomers based on asymmetric carbons at the 1-, 2- and 3-positions of 1,25-dihydroxy-2-methylvitamin D3 derivatives (Maki, et al., 116th (1996) Congress of The Pharmaceutical Society of Japan, Abstract 2, 9).

However, no stereoisomer (20S-form) that is different from natural products regarding the configuration of the carbon atom at the 20-position in 1,25-dihydroxy-2-methylvitamin $D_3$ derivatives being known, there in no information what kinds of influences does the configuration of the carbon atom at the 20-position exert upon a binding affinity to a vitamin D receptor or to a vitamin D bonding protein, or upon other various kinds of above-mentioned biological activities.

In addition, although methods for producing 2-position substituted vitamin $D_3$ derivatives are also described in the above reports, only isomers having specific combinations of configurations of the 1-, 2- and 3-asymmetric carbons among all the combinations of the configurations are disclosed in these reports, and no method for efficiently producing an isomer having an arbitrary combination of the configurations is reported.

Recently, a new method through which an active type of vitamin $D_3$ is synthesized by reacting an exo-methylene compound expressed by the following general formula (II'),

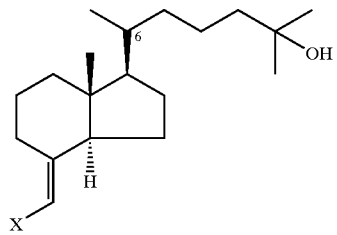

(wherein X is a bromine atom or an iodine atom) with an ene-yne compound expressed by the following general formula (III'),

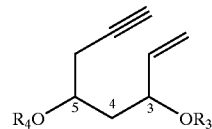

[wherein $R_3$ and $R_4$ are each independently a hydrogen atom or a tri($C_1$ to $C_7$ hydrocarbon)silyl group] has been reported [Trost, B. M., J. Am. Chem. Soc., 114, 9836 (1992)]. However, no one has reported that an ene-yne compound having a substituent such as methyl group at the 4-position is used as the above ene-yne compound.

DISCLOSURE OF INVENTION

It is an object of the present invention to provide a new 1,25-dihydroxy-2-methylvitamin $D_3$ derivative having biological activity and its production method.

According to the present invention, the first object described above of the present invention can be achieved firstly by a 1,25-dihydroxy-2-methylvitamin $D_3$ derivative expressed by the following general formula (I),

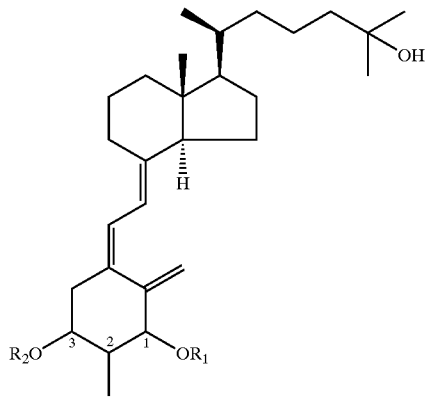

[wherein each of $R_1$ and $R_2$ is independently a hydrogen atom or a tri($C_1$ to $C_7$ alkyl)silyl group; herein configurations of asymmetric carbons at the 1-, 2- and 3-positions are each independently an α-configuration or a β-configuration].

Namely, the vitamin $D_3$ derivatives of the present invention include all of the following 8 kinds of derivatives having the configurations at the 1-, 2- and 3-positions of, (1) the combination of α-configuration, α-configuration and α-configuration, (2) the combination of α-configuration, α-configuration and β-configuration, (3) the combination of α-configuration, β-configuration and α-configuration, (4) the combination of α-configuration, β-configuration and β-configuration, (5) the combination of β-configuration, α-configuration and α-configuration, (6) the combination of β-configuration, α-configuration and β-configuration, (7) the combination of β-configuration, β-configuration and α-configuration, and (8) the combination of β-configuration, β-configuration and β-configuration. Further, a mixture containing any plural isomers out of the 8 stereoisomers at arbitrary ratios is also included in the derivatives of the present invention.

Further, the notation of the configurations used here for vitamin D analogues follows a usual practice. That is, "α-configuration" used at the 1-, 2- and 3-positions means a configuration containing a bond directing the carbon atom from the upper side of the paper and the "β-configuration" means a configuration containing a bond directing the carbon atom from the lower side of the paper.

In addition, according to the present invention, the above-mentioned object of the present invention is achieved secondly by a method for producing a vitamin $D_3$ derivative; expressed by the above formula (I). That is, a 1,25-dihydroxy-2-methylvitamin $D_3$ derivative expressed by the above formula (I) is produced by reacting an exo-methylene compound expressed by the following general formula (II),

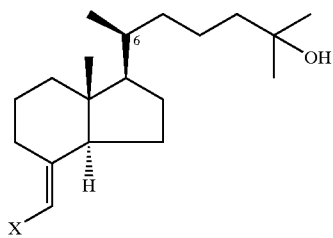

(wherein X is a bromine atom or an iodine atom) with an ene-yne compound expressed by the following general formula (III),

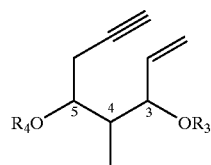

[wherein $R_3$ and $R_4$ are each independently a hydrogen atom or a tri($C_1$ to $C_7$ hydrocarbon)silyl group] in the presence of a palladium catalyst and optionally removing the protecting group of the tri($C_1$ to $C_7$ hydrocarbon)silyl group.

BEST MODE FOR CARRYING OUT THE INVENTION

In the present invention, the tri($C_1$ to $C_7$ alkyl)silyl groups are each a silyl group substituted with independent three straight or branched $C_1$ to $C_7$ alkyl groups, especially preferably a trimethylsilyl, triethylsilyl or t-butyldimethylsilyl group.

Preferred concrete examples of 1,25-dihydroxy-2-methyl-vitamin $D_3$ derivatives expressed by the above formula (1) include
(20S)-1α,25-dihydroxy-2β-methyl-3β-vitamin $D_3$ (68),
(20S)-1β,25-dihydroxy-2β-methyl-3β-vitamin $D_3$ (69),
(20S)-1α,25-dihydroxy-2β-methyl-3α-vitamin $D_3$ (70),
(20S)-1β,25-dihydroxy-2β-methyl-3α-vitamin $D_3$ (71),
(20S)-1α,25-dihydroxy-2α-methyl-3β-vitamin $D_3$ (72),
(20S)-1β,25-dihydroxy-2α-methyl-3β-vitamin $D_3$ (73),
(20S)-1α,25-dihydroxy-2α-methyl-3α-vitamin $D_3$ (74),
(20S)-1β,25-dihydroxy-2α-methyl-3α-vitamin $D_3$ (75)
(20S)-1α,25-dihydroxy-2β-methyl-3β-vitamin $D_3$-1,3-bis(trimethylsilyl)ether (76),
(20S)-1β,25-dihydroxy-2β-methyl-3β-vitamin $D_3$-1,3-bis(trimethyl-silyl)ether (77),
(20S)-1α,25-dihydroxy-2β-methyl-3α-vitamin $D_3$-1,3-bis(trimethyl-silyl)ether (78),
(20S)-1β,25-dihydroxy-2β-methyl-3α-vitamin $D_3$-1,3-bis(trimethyl-silyl)ether (79),
(20S)-1α,25-dihydroxy-2α-methyl-3β-vitamin $D_3$-1,3-bis(trimethyl-silyl)ether (80),
(20S)-1β,25-dihydroxy-2α-methyl-3β-vitamin $D_3$-1,3-bis(trimethyl-silyl)ether (81),
(20S)-1α,25-dihydroxy-2α-methyl-3α-vitamin $D_3$-1,3-bis(trimethyl-silyl)ether (82),
(20S)-1β,25-dihydroxy-2α-methyl-3α-vitamin $D_3$-1,3-bis(trimethyl-silyl)ether (83)
(20S)-1α,25-dihydroxy-2β-methyl-3α-vitamin $D_3$-1,3-bis(t-butyldimethyl-silyl)ether (84),
(20S)-1α,25-dihydroxy-2β-methyl-3β-vitamin $D_3$-1,3-bis(t-butyldimethyl-silyl)ether (85),
(20S)-1α,25-dihydroxy-2β-methyl-3α-vitamin $D_3$-1,3-bis(t-butyldimethyl-silyl)ether (86),
(20S)-1β,25-dihydroxy-2β-methyl-3α-vitamin $D_3$-1,3-bis(t-butyldimethyl-silyl)ether (87),
(20S)-1α,25-dihydroxy-2α-methyl-3β-vitamin $D_3$-1,3-bis(t-butyldimethyl-silyl)ether (88),
(20S)-1α,25-dihydroxy-2α-methyl-3β-vitamin $D_3$-1,3-bis(t-butyldimethyl-silyl)ether (89),
(20S)-1α,25-dihydroxy-2α-methyl-3α-vitamin $D_3$-1,3-bis(t-butyldimethyl-silyl)ether (90), and
(20S)-1β,25-dihydroxy-2α-methyl-3α-vitamin $D_3$-1,3-bis(t-butyldimethyl-silyl)ether (91).

Further, in a method for producing a vitamin $D_3$ derivative expressed by the above formula (I), an ene-yne compound, a starting material, expressed by the above formula (III) may be selected from all the stereoisomers derived from asymmetric carbons at the 3-, 4- and 6-positions, and mixtures of them at arbitrary ratios. Their configurations are held unchanged during reactions, and a 1,25-dihydroxy-2-methylvitamin $D_3$ derivative having the configuration corresponding to the starting material is produced.

A palladium catalyst used in the production method is obtained by combining a zero- or di-valent organic palladium compound with a trisubstituted phosphorus compound. Examples of the organic palladium compound include tetrakis(triphenylphosphine)palladium, tris(dibenzilideneacetone)palladium, tris(dibenzilideneacetone)-palladium-chloroform adduct and palladium acetate. Further, examples of the trisubstituted phosphorous compound include triphenylphosphine and tributylphosphine. As an example of a palladium catalyst prepared by combining both the components, a catalyst having the combination of tris(dibenzilideneacetone) palladium and triphenylphosphine or that of tris (dibenzilideneacetone)palladium-chloroform adduct and triphenylphosphine is preferably cited, and the mixing ratio is preferably (1:1) to (1:10).

Here, the molar ratio of an exo-methylene compound expressed by the above formula (II) to an ene-yne compound expressed by the above formula (III) is preferably in the range from (1:5) to (5:1), and further a palladium catalyst is used in the range of 0.1–100 mol %, preferably 1–20 mol % based on the exo-methylene compound.

Further, as a reaction solvent used in the reaction of an exo-methylene compound expressed by the above formula (II) with an ene-yne compound expressed by the above formula (III), a nonpolar solvent such as hexane, heptane or toluene, a polar solvent such as diethyl ether, tetrahydrofuran, dioxane, dimethoxyethane; N,N-dimethylformamide or acetonitrile, or a mixture of such solvents is cited, and heptane or toluene is preferred among them. Furthermore, when used for the reaction, the solvent is preferably subjected to a pretreatment such as distillation and/or nitrogen displacement, and the reaction is carried out at a temperature in the range from ambient temperature to the boiling point of the solvent.

Further, in order to trap an acid such as a hydrogen halide to be formed in the reaction system, it is preferable to carry out the reaction in the presence of a base e.g. triethylamine or diisopropylethylamine. The amount of the base to be added is preferably one equivalent or more based on the component which is used in a larger equivalent than the other between the reactants expressed by the above formulae (II) and (III).

Among vitamin $D_3$ derivatives of the above formula (I) to be obtained in the above reaction, a compound whose $R_1$ and $R_2$ are each a tri($C_1$–$C_7$ alkyl)silyl group can be converted into a compound whose $R_1$ and $R_2$ are each H by optionally carrying out deprotection reaction.

Such deprotection reaction may be carried out according to a method known per se [for example, Calverley, M. J., Tetrahedron, 43, 4609 (1987); Ho, P. T., Tetrahedron, Letters 1623 (1978)]. Examples of the cleavage agent used here include tetrabutylammonium fluoride, lithium tetrafluoroborate, pyridinium p-toluenesulfonate or camphorsulfonic acid.

Further, an exo-methylene compound expressed by the above formula (II) can be synthesized according to a method known per se (B. Fernandez, et al., J. Org. Chem., 1992, 57, 3173; M. J. Calverley, et al., Chem. Lett., 1993, 3, 1845; A. Kutner, et al., J. Org. Chem., 1988, 53, 3450).

Preferred concrete examples of an ene-yne compound, which are used in the production method of the present invention, expressed by the above formula (III) include (3R,4R,5R)-3,5-dihydroxy-4-methyl-1-octen-7-yne (22), 3S,4R,5R)-3,5-dihydroxy-4-methyl-1-octen-7-yne (23), (3R,4R, 5S)-3,5-dihydroxy-4-methyl-1-octen-7-yne (24), (3S,4R,5S)-3,5-dihydroxy-4-methyl-1-octen-7-yne (25), (3R,4S,5R)-3,5-dihydroxy-4-methyl-1-octen-7-yne (26), (3S,4S,5R)-3,5-dihydroxy-4-methyl-1-octen-7-yne (27), (3R,4S,5S)-3,5-dihydroxy-4-methyl-1-octen-7-yne (28), (3S,4S,5S)-3,5-dihydroxy-4-methyl-1-octen-7-yne (29), (3R,4R,5R)-3,5-bis(trimethylsilyloxy)-4-methyl-1-octen-7-yne (30),
(3S,4R,5R)-3,5-bis(trimethylsilyloxy)-4-methyl-1-octen-7-yne (31),
(3R,4R,5S)-3,5-bis(trimethylsilyloxy)-4-methyl-1-octen-7-yne (32),
(3R,4R,5S)-3,5-bis(trimethylsilyloxy)-4-methyl-1-octen-7-yne (33),
(3R,4R, 5S)-3,5-bis(trimethylsilyloxy)-4-methyl-1-octen-7-yne (34),
(3S,4S,5R)-3,5-bis(trimethylsilyloxy)-4-methyl-1-octen-7-yne (35),
(3R,4S,5S)-3,5-bis(trimethylsilyloxy)-4-methyl-1-octen-7-yne (36),
(3S,4S,5S)-3,5-bis(trimethylsilyloxy)-4-methyl-1-octen-7-yne (37),
(3R,4R,5R)-3,5-bis(t-butyldimethylsilyloxy)-4-methyl-1-octen-7-yne (38)
(3S,4R,5R)-3,5-bis(t-butyldimethylsilyloxy)-4-methyl 1-octen-7-yne (39),
(3R,4R,5S)-3,5-bis(t-butyldimethylsilyloxy)-4-methyl-1-octen-7-yne (40),
(3S,4R,5S)-3,5-bis(t-butyldimethylsilyloxy)-4-methyl-1-octen-7-yne (41),
(3R,4S,5R)-3,5-bis(t-butyldimethylsilyloxy)-4-methyl-1-octen-7-yne (42),
(3S,4R,5S)-3,5-bis(t-butyldimethylsilyloxy)-4-methyl-1-octen-7-yne (43),
(3R,4S,5S)-3,5-bis(t-butyldimethylsilyloxy)-4-methyl-1-octen-7-yne (44) and
(3S,4S,5S)-3,5-bis(t-butyldimethylsilyloxy)-4-methyl-1-octen-7-yne (45).

An ene-yne compound, which is expressed by the above formula (III) and used in the production method of the present invention, can be synthesized, for example, by the following Scheme 1.

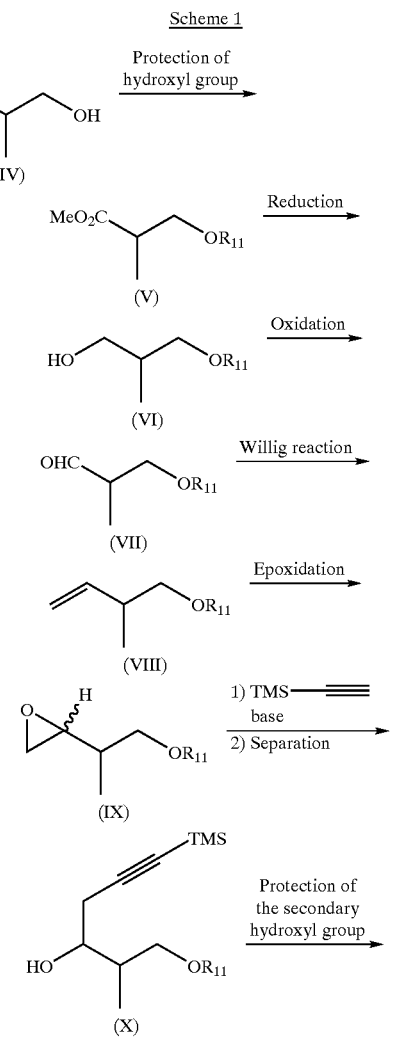

Scheme 1

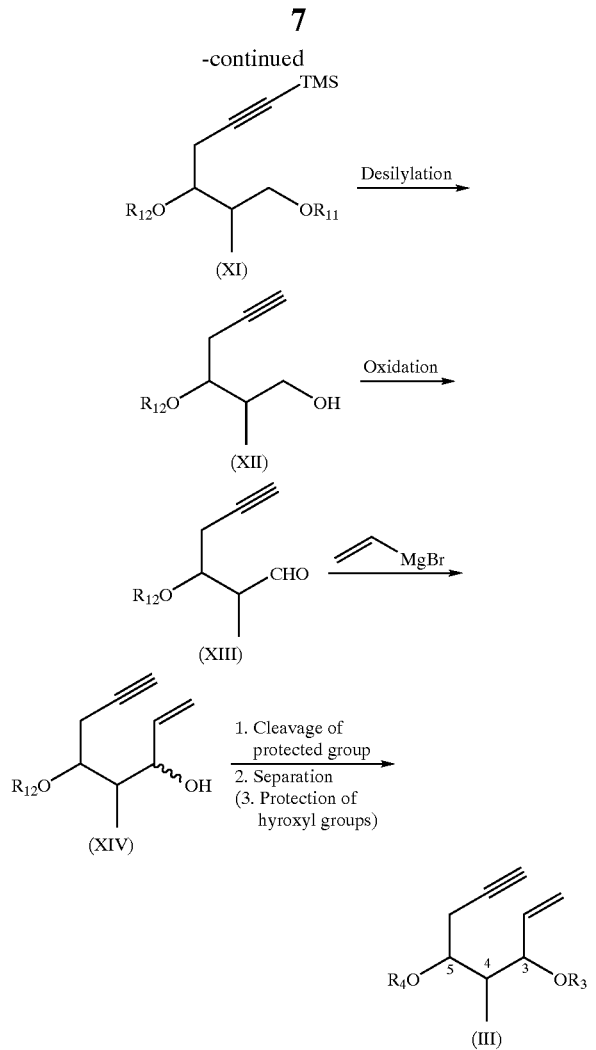

In the above scheme 1, $R_{11}$ is a tri($C_1$ to $C_7$ alkyl)silyl group or a ($C_1$ to $C_7$ alkyl)di($C_6$ to $C_{10}$ aryl)silyl group, and preferred examples of $R_{11}$ include trimethylsilyl, triethylsilyl, t-butyldimethylsilyl and t-butyldiphenylsilyl groups. Further, $R_{12}$ is a protecting group which together with an oxygen atom bonded to the $R_{12}$ forms an acetal, and methoxymethyl, methoxyethoxymethyl and tetrahydropyranyl groups are suitable as the $R_{12}$.

This production is carried out as follows. At first, the hydroxyl group of a commercially available optically active ester compound (IV) is protected by a silyl group in the presence of a base to obtain a compound (V). As the silylating agent used here, triethylsilyl chloride, t-butyldimethylsilyl chloride, t-butyldiphenylsilyl chloride, triethylsilyl triflate, t-butyldimethylsilyl triflate, etc., is preferably used. Further, as the base of the reaction, a common base such as triethylamine, 2,6-lutidine or imidazole is used.

Subsequently, the compound (V) is reduced with a hydride-type reducing agent to obtain an alcohol (VI). As the hydride-type reducing agent, lithium aluminum hydride, diisobutylaluminum hydride, etc., is preferable. The produced hydroxyl group is oxidized with dimethyl sulfoxide/oxalyl chloride, TPAP (tetrapropylammonium perruthenate)/N-methylmorpholine-N-oxide, etc., to obtain an aldehyde (VII), and subjecting the obtained aldehyde (VII) to a common Witting reaction to obtain a methylene compound (VIII).

Subsequently, the resultant double bond is oxidized with a peroxide such as hydrogen peroxide or m-chloroperbenzoic acid to obtain an epoxide compound (IX) and, the obtained epoxide compound is made to react with an acetylene derivative shown in the above scheme in the presence of a base such as alkyl lithium to obtain a compound (X). The compound (X) is formed as a (1:1) mixture of a pair of diastereomers based on the stereoisomerism of the hydroxyl group of the compound (X), while these diastereomers can easily be separated and purified by an ordinary separation process such as column chromatography. Further, configurations of the hydroxyl groups of the separated diastereomers can be determined by measuring $^1$H-NMR after converting the separated diastereomers to MTPA esters of (R)- and (S)-types [Kusumi, et al., Journal of Synthetic Organic Chemistry, JAPAN, 51, 462 (1996)].

Further, each of the separated compounds (X) is subjected to the following reactions to produce an objective ene-yne compound expressed by the above formula (III) in an optically pure state. That is, the hydroxyl group of a compound (X) is protected with an acetal to obtain a compound (XI). As the acetal-forming agent, methoxymethyl chloride, methoxyethoxymethyl chloride, dihydropyran, etc., is used. Then, the compound (XI) is treated with a fluoride agent such as tetrabutylammonium fluoride to give a desilylated compound (XII), and the resultant primary hydroxyl group is oxidized with dimethyl sulfoxide/oxalyl chloride, TPAP (tetrapropylammonium perruthenate)/N-methylmorpholine-N-oxide, etc., to form an aldehyde (XIII). Further, the aldehyde group is made to react with a vinyl Grignard reagent to obtain a compound (XIV). Finally, the acetal-type protecting group for the hydroxyl group at the 5-position is removed under an acidic condition to obtain the objective ene-yne compound (III).

The compound (III) is formed as a (1:1) mixture of two kinds of diastereomers based on the stereoisomerism of the hydroxyl group at the 3-position, while these diastereomers can be easily separated and purified by an ordinary separation process such as column chromatography. Further, the configuration of the hydroxyl group of the separated diastereomers can be determined by measuring $^{13}$C-NMR after converting the separated diastereomers to acetonide compounds derived from the 3- and 5-hydroxyl groups [Rychnovsky, S. D., J. Org. Chem., 58, 3511 (1993)]. Furthermore, if necessary, the hydroxyl groups at the 3- and the 5-positions can be protected is with silyl groups.

As the silylating agent used here, trimethylsilyl chloride, triethylsilyl chloride, t-butyldimethylsilyl chloride, t-butyldiphenylsilyl chloride, triethylsilyl triflate, t-butyldimethylsilyl triflate, etc., is preferably used, and as the base of the reaction, a common base such as triethylamine, 2,6-lutidine or imidazole is used. The reaction conditions, a solvent, a reaction temperature, etc., of each reaction process in the above reactions are those which are commonly used in such a reaction process.

In the production method, the configuration of the methyl group at the 4-position of the objective ene-yne compound (III) is derived from an optically active ester compound (IV) as the starting material (IV), and in the synthetic rout of the present invention, the configuration is held through all the reactions. That is, an important intermediate (III) for the synthesis of vitamins $D_3$ can be produced in an optically pure state by using an optically active ester compound (IV) as the starting material and consistently adapting reactions capable of holding the configuration.

As examples of the method for producing an optically pure ene-yne compound, synthetic methods for (3R,4R,5R)-3,5-bis(t-butyldimethylsilyloxy)-4-methyl-1-octen-7-yne (38) and (3S,4R,5R)-3,5-bis(t-butyldimethylsilyloxy)-4- methyl-1-octen-7-yne (39) are shown by the following schemes. 2 and 3, respectively.
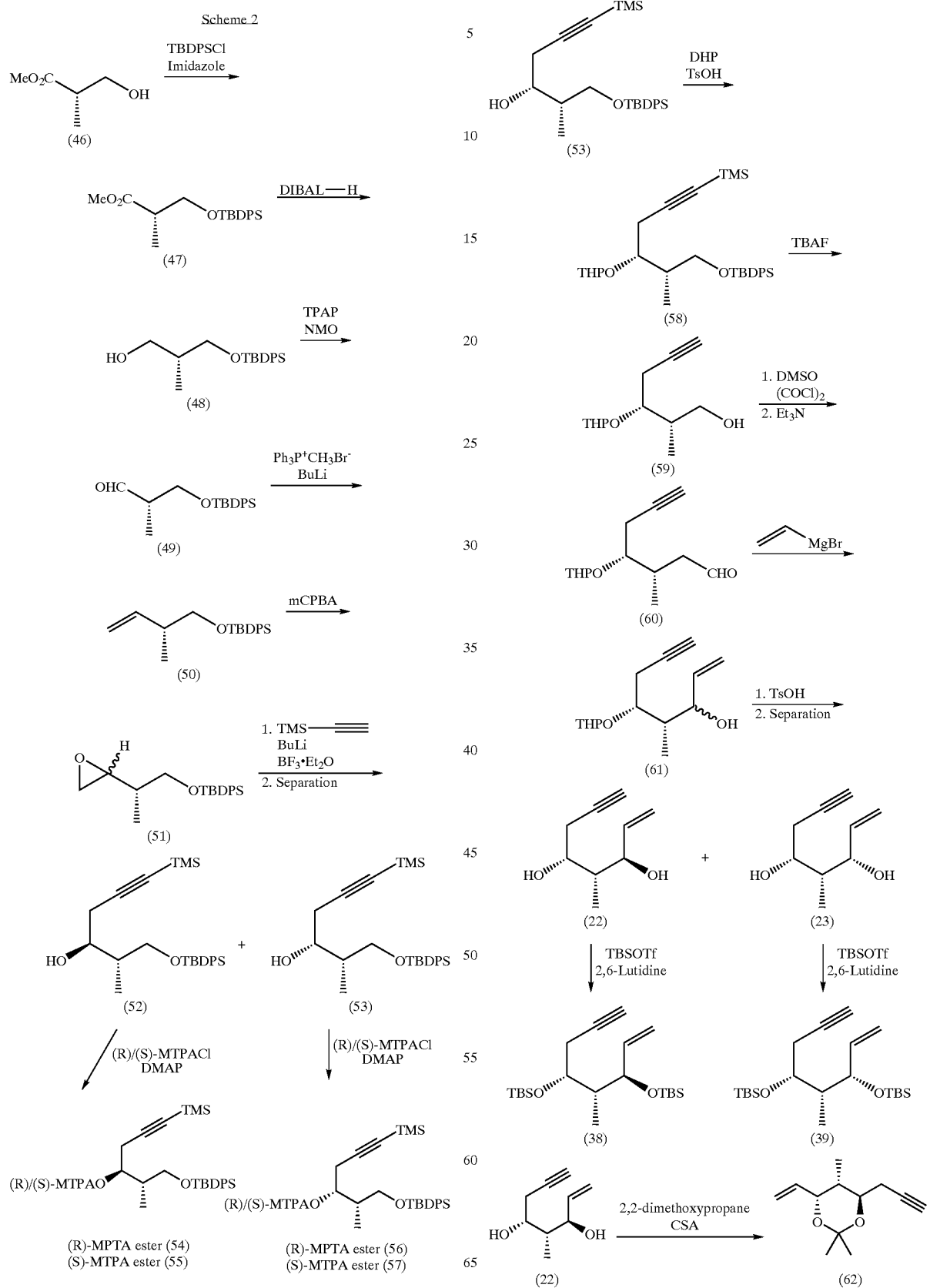

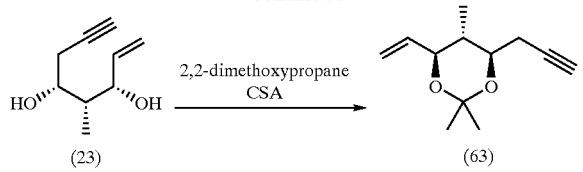

[in the above schemes, TBDPSCl is t-butyldiphenylsilyl chloride, DIBAL-H is diisobutylaluminum hydride, TPAP is tetrapropyl-ammonium perruthenate, NMO is N-methylmorpholine-N-oxide, mCPBA is m-chloroperbenzoic acid, MTPACl is α-methoxy-α-(trifluoromethyl)phenylacetyl chloride, DMAP is 4-(dimethyl-amino)pyridine, DHP is dihydropyran, TsOH is p-toluenesulfonic acid, TBAF is tetrabutylammonium fluoride and TBSOTf is t-butyldimethylsilyl triflate, TBDPS is a t-butyldiphenylsilyl group, TBS is a t-butyldimethylsilyl group and THP is a tetrahydropyranyl group].

Besides, these examples, e.g. a compound of (4R,5S)-series can be synthesized by a similar production method using a compound (52) obtained through the above scheme 2, and a compound of (4S)-series can be synthesized by a similar production method using the following optically active ester (64), as the starting material respectively.

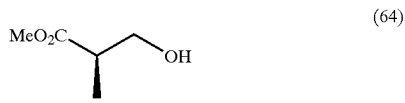

EXAMPLES

The present invention will be explained further in detail hereafter with examples, while the present invention is not restricted by the examples.

At first, preparations of compounds of the above-mentioned formula (III), which are synthetic intermediates of compounds of the present invention, are described as reference examples.

Reference Example 1

Synthesis of methyl(S)-3-(t-butyldiphenylsilyloxy)-2-methylpropionate (47)

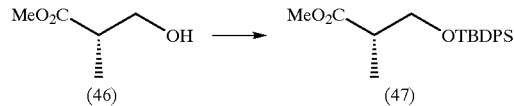

Under argon atmosphere, Methyl(S)-3-hydroxy-2-methyl-propionate (46) (1.9 ml, 2.0 g, 16.9 mmol) was dissolved in 100 ml of dichloromethane, imidazole (2.3 g, 32.5 mmol) and TBDPSCl (4.3 ml, 16.9 mmol) were added to the resultant solution, and the mixture was stirred for 5 min. The reaction mixture was extracted with ethyl acetate after the addition of H$_2$O. The ethyl acetate layer was washed with brine, dried over magnesium sulfate and evaporated. The obtained crude product was purified by column chromatography (60 g, 2% AcOEt-hexane) to obtain a colorless oily product (47) (6.5 g, quant.).

$^1$H-NMR (400 MHz, CDCl$_3$/TMS) δ: 1.04 (9H, s), 1.15 (3H, d, J=7.0 Hz), 2.72 (1H, dquin, J=5.8, 7.0 Hz), 3.67 (3H, s), 3.73 (1H, dd, J=6.4, 9.8 Hz), 3.83 (1H, dd, J=9.8, 6.4 Hz), 1.35–7.44 (6H, m), 7.64–7.68 (4H, m).

MS m/z: 325 (M$^+$-Me—Me), 299 (M$^+$-tBu).

Reference Example 2

Synthesis of (R)-3-(t-butyldiphenylsilyloxy)-2-methylpropanol (48)

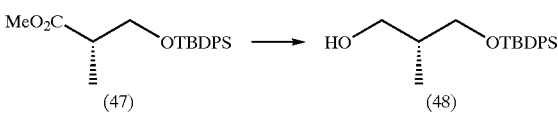

Under argon atmosphere, Methyl(S)-3-(t-butyldiphenylsilyloxy)-2-metylpropionate (47) (1.0 g, 2.7 mmol) was dissolved in 50 ml of dry toluene, 1M DIBAL-H/hexane (5.7 ml, 5.7 mmol) was added to the resultant solution at 0° C., and the mixture was stirred for 15 min. Subsequently, the reaction mixture was further stirred for 45 min after the temperature was returned to room temperature. Ethyl acetate was added to the reaction mixture to decompose the excess DIBAL-H, and the resultant mixture was extracted with 0.5N HCl. The ethyl acetate layer was washed with brine, dried over magnesium sulfate and evaporated. The obtained crude product was purified by column chromatography (30 g, 4–10% AcOEt-hexane) to obtain a colorless oily product (48) (968 mg, quant.).

$^1$H-NMR (400 MHz, CDCl$_3$/TMS) δ: 0.83 (3H, d, J=7.0 Hz), 1.06 (9H, s), 1.99 (1H, ddddq, J=4.6, 5.2, 6.2, 7.0 Hz), 2.58 (1H, bs), 3.60 (1H, dd, J=7.6, 10.1 Hz), 3.97 (2H, d, J=6.4 Hz), 3.72 (1H, dd, J=4.6, 10.1 Hz), 7.37–7.46 (6H, m), 7.67-7.69 (4H, m).

MS m/z: 328 (M$^+$), 271(M$^+$-tBu).

Reference Example 3

Synthesis of (S)-3-(t-butyldiphenylsilyloxy)-2-methylpropanal (49)

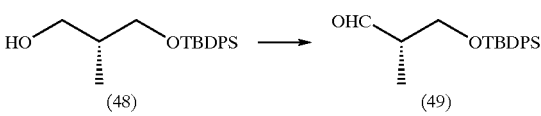

Under argon atmosphere, (R)-3-(t-butyldiphenylsilyloxy)-2-methylpropanol (48) (725 mg, 2.2 mmol) was dissolved in 40 ml of dry dichloromethane. MS-4A (30 mg), NMO (862 mg, 11.1 mmol) and TPAP (catalytic amount) were added to the resultant solution at 0° C., and the mixture was stirred for 15 min. The reaction mixture was further stirred overnight after the temperature was returned to room temperature. Subsequently, H$_2$O was added to the reaction mixture, and the mixture was extracted with ethyl acetate. The ethyl acetate layer was washed with brine, dried over magnesium sulfate and evaporated. The obtained crude product was purified by column chromatography (21 g, 4% AcOEt-hexane) to obtain a colorless oily product (49) (700 mg, 97%).

$^1$H-NMR (400 MHz, CDCl$_3$/TMS) δ:1.04 (9H, s), 1.10 (3H, d, J=7.0 Hz), 2.56 (1H, ddddq, J=1.3, 4.8, 6.1, 7.0 Hz), 3.87 (2H, ddd, J=4.8, 6.1, 10.0 Hz), 7.36-7.46 (6H, m), 7.63–7.67 (4H, m), 9.77 (1H, d, J=1.5 Hz).

MS m/z: 325 (M$^+$-H), 269 (M$^+$-tBu).

Reference Example 4

Synthesis of (S)-4-(t-butyldiphenylsilyloxy)-3-methyl-1-butene (50)

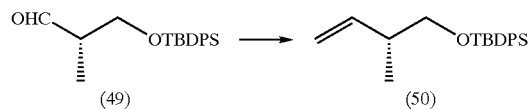

Under argon atmosphere, Ph$_3$P$^+$CH$_3$Br (2.2 g, 7.4 mmol) was suspended in 15 ml of THF, butyllithium (5.2 ml, 9.3 mmol) was added to the resultant solution at 0° C., and the mixture was stirred for 20 min. The treated mixture was added to a 15-ml THF solution of (S)-3-(t-butyldiphenylsilyloxy)-2-methylpropanal (49) (1.2 g, 3.7 mmol) at 0° C. The resultant mixture was stirred for 15 min and further for 45 min after the temperature was returned to room temperature. Then, the reaction mixture was extracted with ethyl acetate after the addition of a saturated ammonium chloride aqueous solution. The ethyl acetate layer was washed with brine, dried over magnesium sulfate, and evaporated. The crude product was purified by column chromatography (12 g, 2% AcOEt-hexane) to obtain a colorless oily product (50) (1.1 g, 92%).

$^1$H-NMR (400 MHz, CDCl$_3$/TMS) δ: 1.03 (3H, d, J=7.0 Hz), 1.05 (9H, s), 2.39 (1H, ddq, J=6.0, 6.7, 7.0 Hz), 3.49 (1H, dd, J=6.7, 9.7 Hz), 3.57 (1H, dd, J=6.1, 9.7 Hz), 5.01 (3H, m), 7.35–7.44 (6H, m), 7.65–7.68 (4H, m), 9.77 (1H, d, J=1.5 Hz).

MS m/z: 267 (M$^+$-tBu).

Reference Example 5

Synthesis of (3S)-4-(t-butyldiphenylsilyloxy)-3-methyl-1-butene oxide (51)

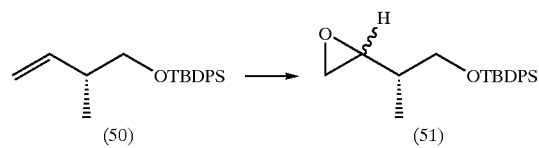

Under argon atmosphere, (S)-4-(t-butyldiphenylsilyloxy)-3-methyl-1-butene (50) (1.0 g, 3.1 mmol) was dissolved in 25 ml of dry dichloromethane, mCPBA (1.4 g, 7.4 mmol) was added to the resultant solution at 0° C., and the mixture was stirred for 15 min. Then, the mixture was further stirred overnight after the temperature was returned to room temperature. The reaction mixture was extracted with ethyl acetate after the addition of water. The ethyl acetate layer was washed with brine, dried over magnesium sulfate and evaporated. The obtained crude product was purified by column chromatography (30 g, 2% Et$_2$O-hexane) to obtain a colorless oily product (51). (1.1 g, quant.).

$^1$H-NMR (400 MHz, CDCl$_3$/TMS) δ: 0.99 (3H, d, J=6.8 Hz), 1.05 (5H, s), 1.07 (4H, s), 1.58 (1H, dtq, J=5.0, 6.7, 7.0 Hz), 2.57 (4/9H, m), 2.60 (8/9H, dd, J=2.7, 5.0 Hz), 2.73 (4/9H, dd, J=4.3, 5.0 Hz), 2.76 (5/9H, dd, J=4.3, 5.0 Hz), 2.85 (5/9H, ddd, J=2.7, 4.3, 7.0 Hz), 2.97 (4/9H, ddd, J=2.7, 4.3, 7.0 Hz), 3.49 (1H, dd, J=6.7, 9.7 Hz), 3.62 (1H, dd, J=7.0, 9.7 Hz), 3.70 (1H, dd, J=5.0, 9.7 Hz), 4.02 (3H, m), 7.39 (6H, m), 7.67 (4H, m).

MS m/z: 283 (M$^+$-tBu).

Reference Example 6

Syntheses of (2S,3S)-1-(t-butyldiphenylsilyloxy)-2-methyl-6-tri-methylsilyl-5-hexyn-3-ol (52) and (2S,3R)-1-(t-butyldiphenylsilyl-oxy)-2-methyl-6-trimethylsilyl-5-hexyn-3-ol (53)

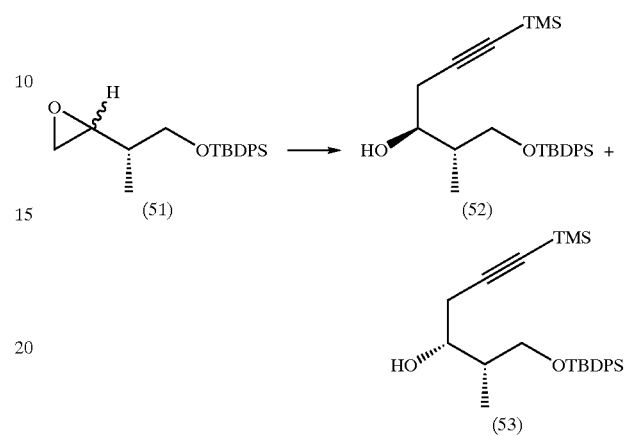

Under argon atmosphere, ethynyltrimethylsilane (0.78 ml, 5.0 mmol) was dissolved in 40 ml of THF, and butyllithium (4.5 ml, 5.0 mmol) was added to the resultant solution at 0° C., and the mixture was stirred for 20 min. The treated mixture was cooled to −78° C. and added to 40 ml THF solution of the compound (51) (1.7 g, 5.0 mmol). The resultant mixture was stirred at −78° C. for 15 min after the addition of BF$_3$.Et$_2$O (9.5 ml, 5.0 mmol), and further for 2 hr after the temperature was returned to room temperature. The reaction mixture was extracted with ethyl acetate after the addition of a saturated ammonium chloride aqueous solution. The ethyl acetate layer was washed with brine, dried over magnesium sulfate and evaporated. The obtained crude product was purified by column chromatography (51 g, 2% Et$_2$O-hexane) to obtain a product (52) (1.2 g, 52%) and a product (53) (1.1 g, 49%), both as colorless oily substances.

52

$^1$H-NMR (400 MHz, CDCl$_3$/TMS) δ: 0.14 (9H, s), 1.00 (3H, d, J=7.0 Hz), 1.06 (9H, s), 1.92–1.99 (1H, m), 2.42 (1H, dd, J=7.0, 10.1 Hz), 2.50 (1H, dd, J=6.7, 10.1 Hz), 2.84 (1H, d, J=3.1 Hz), 3.67 (1H, dd, J=6.4, 10.2 Hz), 3.75 (1H, dd, J=4.2, 10.2 Hz), 3.79 (1H, dd, J=4.3, 10.4 Hz), 7.37–7.46 (6H, m), 7.65–7.68 (4H, m).

MS m/z: 381 (M$^+$-tBu), 269 (M$^+$-Me-2Ph), 239 (M$^+$-2Ph-3Me).

53

$^1$H-NMR (400 MHz, CDCl$_3$/TMS) δ: 0.15 (9H, s), 0.91 (3H, d, J=7.1 Hz), 1.07 (9H, s), 1.93–1.99 (1H, m), 2.46 (1H, dd, J=6.4, 10.6 Hz), 2.54 (1H, dd, J=6.4, 10.6 Hz), 2.84 (1H, d, J=3.1 Hz), 3.67 (1H, dd, J=6.4, 10.4 Hz), 3.74–3.76 (1H, m), 3.79 (1H, dd, J=4.3, 10.4 Hz), 7.37–7.46 (6H, m), 7.65–7.68 (4H, m).

MS m/z: 423 (M$^+$-Me), 365 (M$^+$-TMS), 308 (M$^+$-TMS-tBu).

Reference Example 7

Syntheses of MTPA Esters [Determination of the Absolute Configuration of an Alcohol (X)]

Under argon atmosphere, each of the above alcohols (X) was dissolved in dry dichloromethane. DMPA (2 equivalent)

and (R)- or (S)-MTPAC1 (2 equivalent) were added to the resultant solution, and the mixture was stirred at room temperature for 4 hr. The reaction mixture was purified on TLC (10% AcOEt-hexane) without having any pretreatment to obtain the corresponding MTPA ester.

Syntheses of Compounds (54) and (55) from the Compound (52)

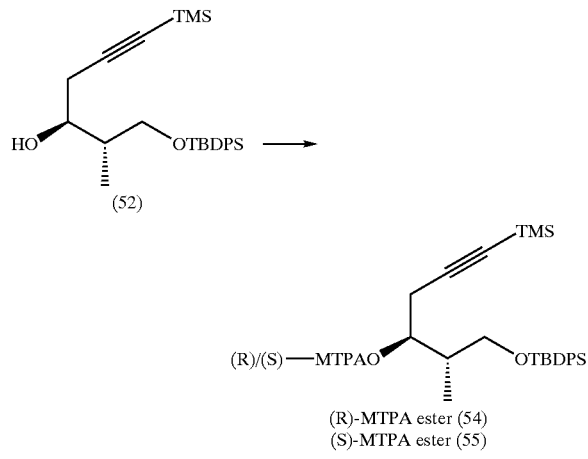

54(R)
Yield: 30% (colorless oil).
$^1$H-NMR (400 MHz, CDCl$_3$/TMS) δ: 0.12 (9H, s), 0.80 (3H, d, J=6.7 Hz), 1.06 (9H, s), 2.17 (1H, q, J=6.7 Hz), 2.68 (1H, t, J=6.7 Hz), 3.41 (2H, dd, J=3.0, 10.3 Hz), 3.58 (3H, s), 5.46 (1H, dd, J=6.1, 10.3 Hz), 7.28–7.46 (9H, m), 7.49–7.55 (2H, m), 7.61–7.65 (4H, m).

55(S)
Yield: 25% (colorless oil).
$^1$H-NMR (400 MHz, CDCl$_3$/TMS) δ: 0.12 (9H, s), 0.86 (3H, d, J=7.0 Hz), 1.07 (9H, s), 2.28 (1H, q, J=6.1 Hz), 2.57 (1H, dd, J=5.8, 10.6 Hz), 2.71 (1H, dd, J=6.1, 10.6 Hz), 3.46 (3H, s), 3.48 (2H, m), 5.49 (1H, dd, J=5.8, 9.8 Hz), 7.28–7.46 (9H, m), 7.49–7.56 (3H, m), 7.60–7.69 (4H, m).

Syntheses of Compounds (56) and (57) from the Compound (53)

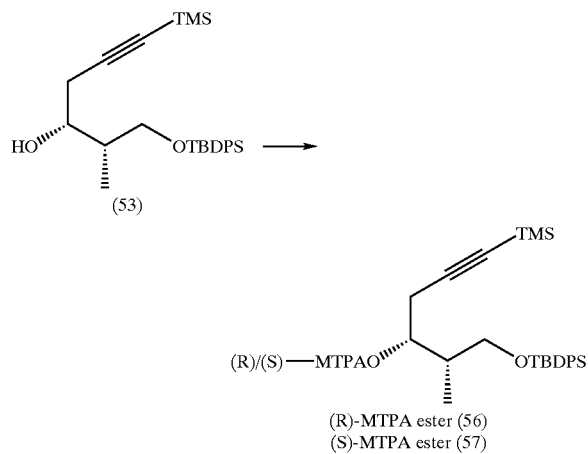

56(R)
Yield: 13% (colorless oil).
$^1$H-NMR (400 MHz, CDCl$_3$/TMS) δ: 0.07 (9H, s), 0.95 (3H, d, J=7.0 Hz), 1.05 (9H, s), 2.26 (1H, q, J=6.7 Hz), 2.55 (1H, dd, J=6.1, 11.6 Hz), 2.75 (1H, dd, J=5.2, 11.6 Hz), 3.42 (3H, s), 3.56 (1H, dd, J=5.8, 10.7 Hz), 3.64 (1H, dd, J=6.5, 10.7 Hz), 5.27 (1H, dd, J=5.8, 11.6 Hz), 7.28–7.45 (9H, m), 7.50–7.56 (2H, m), 7.59–7.65 (4H, m).

57(S)
Yield: 17% (colorless oil).
$^1$H-NMR (400 MHz, CDCl$_3$/TMS) δ: 0.11 (9H, s), 0.82 (3H, d, J=7.0 Hz), 1.05 (9H, s), 2.19 (1H, q, J=6.1 Hz), 2.58 (1H, dd, J=6.7, 11.0 Hz), 2.75 (1H, dd, J=6.7, 11.0 Hz), 3.49 (1H, dd, J=5.4, 10.3 Hz), 3.54 (1H, dd, J=5.8, 10.3 Hz), 3.57 (3H, s), 5.32 (1H, dd, J=6.7, 10.3 Hz), 7.28–7.45 (9H, m), 7.54–7.59 (2H, m) 7.59–7.65 (4H, m).

Reference Example 8

Synthesis of (4R,5S)-6-(t-butyldiphenylsilyloxy)-5-methyl-4-tetrahydropyranyloxy-1-trimethylsilyl-1-hexyne (58)

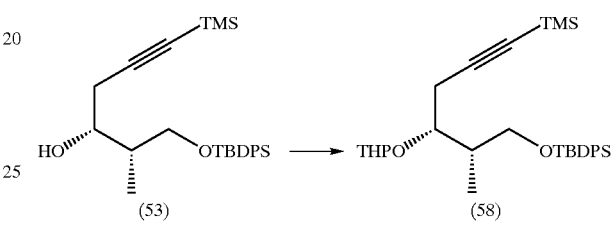

DHP (0.34 ml, 3.75 mmol, 1.05 equivalent) and TsOH (72 mg, 0.375 mmol, 0.15 equivalent) were added to a dichloromethane solution (10 ml) of the alcohol (53) (1.07 g, 2.50 mmol), and the mixture was allowed to stand overnight at room temperature. A saturated sodium bicarbonate aqueous solution was added to the reaction mixture, and the resultant mixture was extracted with ethyl acetate. The extract was washed with brine, dried over magnesium sulfate and evaporated. The obtained crude product was purified by silica gel column chromatography (100 g, 1% AcOEt-hexane) to obtain a colorless oily product (58) (1.26 g, 98%).

$^1$H-NMR (400 MHz, CDCl$_3$TMS) δ: 0.127 (9/2H, s), 0.135 (9/2H, s), 0.95 (3H, d, J=7.0 Hz), 1.058 (9/2H, s), 1.061 (9/2H, s), 1.41–1.62 (4H, m), 1.69–1.81 (2H, m>, 2.09–2.17 (1H, m), 2.38 (1/2H, dd, J=7.3, 17.1 Hz), 2.46 (1/2H, dd, J=4.6, 17.1 Hz), 2.54 (1/2H, dd, J=5.5, 17.1 Hz), 2.66 (1/2H, dd, J=5.8, 17.1 Hz), 3.38–3.49 (1H, m), 3.58–3.71 (2H, m), 3.75–3.81 (1H, m), 3.88–3.91 (1/2H, m), 3.92–4.06 (1/2H, m), 4.66 (1/2H, dd, J=3.1, 3.4 Hz), 4.86 (1/2H, dd, J=2.7, 4.3 Hz), 7.35–7.44 (6H, m>, 7.65–7.70 (4H, m).

Reference Example 9

Synthesis of (2S, 3R)-2-methyl-3-tetrahydropyranyloxy-5-hexyn-1-ol (59)

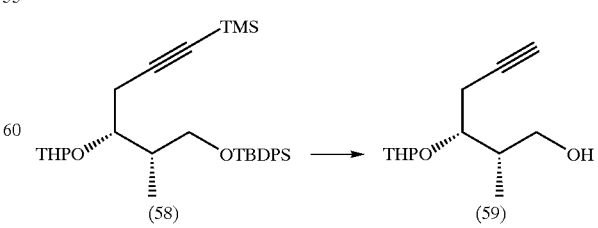

A 1M nBu$_4$NF/THF solution (8.8 ml, 8.80 mmol, 4 equivalent) was added to a THF solution (20 ml) of the compound (58) (1.13 g, 2.20 mmol), and the mixture was stirred at room temperature for 4 hr. The reaction mixture was extracted with ethyl acetate after the addition of water. The extract was washed with brine, dried over magnesium sulfate and evaporated. The obtained crude product was purified by silica gel column chromatography (35 g, 20% AcOEt-hexane) to obtain a colorless oily product (59) (450 mg, 96%). $^1$H-NMR (400 MHz, CDCl$_3$/TMS) δ: 0.99 (3/2H, d, J=6.7 Hz), 1.01 (3/2H, d, J=7.0 Hz), 1.41–1.89 (6H+1/2H, m), 1.99 (1/2H, t, J=2.7 Hz), 2.00 (1/2H, t, J=2.7 Hz), 2.13–2.19 (1/2H, m), 2.33 (1/2H, bs), 2.38 (1/2H, ddd, J=2.4, 6.1, 17.1 Hz), 2.57 (1/2H, ddd, J=2.4, 4.0, 17.1 Hz), 2.63 (1/2H, ddd, J=2.8, 4.0, 17.1 Hz), 2.72 (1/2H, ddd, J=2.8, 7.0, 17.1 Hz), 3.30–3.31 (1/2H, m), 3.41–3.56 (3/2H, m), 3.60–3.81 (2H, m>, 3.95–4.01 (3/2H, m), 4.69–4.71 (1H, m).

Reference Example 10

Synthesis of (4R,5R)-3-hydroxy-4-methyl-5-tetrahydropyranyloxy-1-octen-7-yne (61)

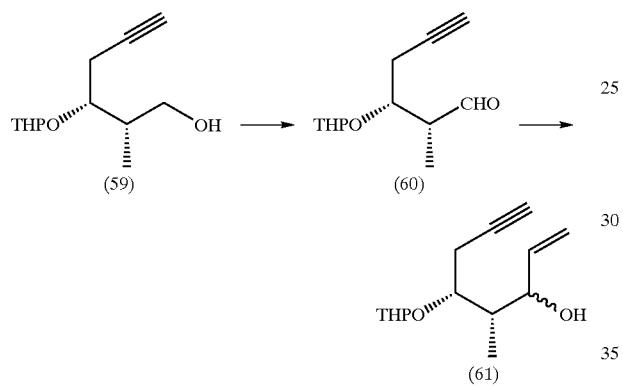

Oxalyl chloride (0.56 ml, 6.30 mmol, 3 equivalent) was added to a dichloromethane solution (4 ml) of DMSO (0.92 ml, 12.5 mmol, 6 equivalent), and the mixture was stirred at −78° C. for 1 hr under argon atmosphere. A dichloromethane solution (10 ml) of the compound (59) (440 mg, 2.08 mmol) was added to the resultant solution at −78° C., and the mixture was stirred for 30 min. Subsequently, Et$_3$N (3.2 ml, 24 mmol, 12 equivalent) was added to the mixture followed by stirring for 1 hr, while the temperature was elevated from −78° C. to 0° C. The reaction mixture was extracted with ethyl acetate after the addition of water, the extract was washed with brine, dried over magnesium sulfate and evaporated. The resultant crude product was filtered through a short column of silica gel, and the filtrate was evaporated to obtain a colorless oily aldehyde (60). The product (60) was used for the next reaction without further purification.

A 1M vinyl magnesium bromide/THF solution (4.0 ml, 4.00 mmol, 2 equivalent) was added to a THF solution (10 ml) of the aldehyde (60) (426 mg, 2.02 mmol) at 0° C. the mixture was stirred at 0° C. for 1 hr. The reaction mixture was extracted with ethyl acetate after the addition of water. The extract was washed with brine, dried over magnesium sulfate and evaporated. The obtained crude product was purified by silica gel column chromatography (55 g, 20% AcOEt-hexane) to obtain a colorless oily allyl alcohol (61) (329 mg, 68%).

$^1$H-NMR (400 MHz, CDCl$_3$/TMS) δ: 0.85 (3/4H, d, J=7.0 Hz), 0.88 (3/4H, d, J=7.3 Hz), 0.90 (3/4H, d, J=7.0 Hz), 0.93 (3/4H, d, J=7.0 Hz), 1.47–1.87 (6H, m), 1.98–2.05 (1H, m>, 2.15–2.19 (1H, m), 2.37–2.89 (2H, m), 3.37–4.15 (4.5H, m), 4.51–4.84 (1.5H, m), 5.13–5.35 (2H, m), 5.83–5.94 (1H, m).

Reference Example 11

Syntheses of (3R,4R,5R)-3,5-dihydroxy-4-methyl-1-octen-7-yne (22) and (3S,4R,5R)-3,5-dihydroxy-4-methyl-1-octen-7-yne (23)

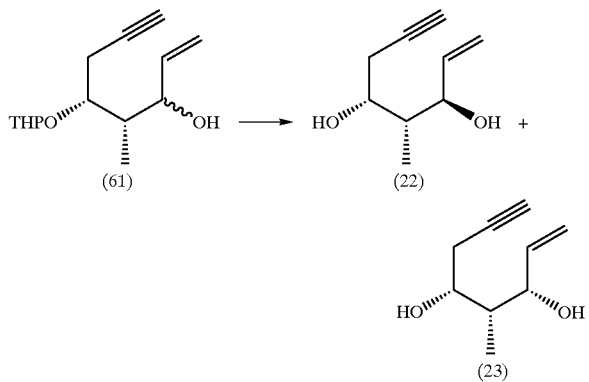

TsOH (25 mg, 0.13 mmol, 0.1 equivalent) was added to a methanol solution (10 ml) of the allyl alcohol (61) (315 mg, 1.32 mmol), and the mixture was allowed to stand at room temperature for 1 hr. The reaction mixture was extracted with Et$_2$O after the addition of a saturated bicarbonate aqueous solution. The extract was washed with brine, dried over magnesium sulfate and evaporated. The obtained crude product was purified by silica gel column chromatography (55 g, 10% AcOEt-hexane) to obtain a colorless oily ene-yne compound (22) (79 mg, 39%) and a colorless oily ene-yne compound (23) (75 mg, 37%).

22

$^1$H-NMR (400 MHz, CDCl$_3$/TMS) δ: 0.90 (3H, d, J=7.0 Hz), 1.95 (1H, dquin, J=2.8, 7.0 Hz), 2.08 (1H, t, J=2.8 Hz), 2.43 (1H, ddd, J=2.8, 7.0, 17.1 Hz), 2.54 (1H, ddd, J=2.8, 4.6, 17.1 Hz), 2.72 (1H, d, J=5.5 Hz), 2.96 (1H, d, J=4.6 Hz), 3.79 (1H, tt, J=4.6, 7.0 Hz), 4.44 (1H, dtt, J=7.0, 1.5, 5.5 Hz), 5.23 (1H, dt, J=10.7, 1.5 Hz), 5.32 (1H, dt, J=17.1, 1.5 Hz), 5.94 (1H, ddd, J=5.5, 10.7, 17.1 Hz).

23

$^1$H-NMR (400 MHz, CDCl$_3$/TMS) δ: 0.83 (3H, d, J=7.0 Hz), 1.83 (1H, dquin, J=7.0, 7.9 Hz), 2.07 (1H, t, J=2.8 Hz), 2.41 (1H, ddd, J=2.8, 6.7, 16.8 Hz), 2.58 (1H, ddd, J=2.8, 4.0, 16.8 Hz), 2.88 (1H, bs), 3.41 (1H, bs), 3.74 (1H, m), 4.14 (1H, tt, J=1.2, 7.3 Hz), 5.19 (1H, dt, J=10.4, 1.2 Hz), 5.27 (1H, dt, J=17.1, 1.2 Hz), 5.88 (1H, ddd, J=7.3, 10.4, 17.1 Hz).

Reference Example 12

Synthesis of (3R,4R,5R)-3,5-bis(t-butyldimethylsilyloxy)-4-methyl-1-octen-7-yne (38)

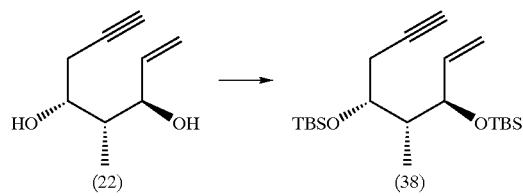

2,6-Lutidine (0.18 ml, 1.5 mmol, 0.4 equivalent) and subsequently TBSOTf (0.34 ml, 1.5 mmol, 4 equivalent) were added to dichloromethane solution (5 ml) of the compound (22) (58 mg, 0.376 mmol), and the mixture was stirred at 0° C. for 1 hr. The reaction mixture was extracted with ethyl acetate after the addition of a saturated bicarbonate aqueous solution. The extract were washed with brine, dried over magnesium sulfate and evaporated. The obtained crude product was purified by silica gel column chromatography (10 g, 2% AcOEt-hexane) to obtain a colorless oily ene-yne compound (38) (141 mg, 98%).

$^1$H-NMR (400 MHz, CDCl$_3$/TMS) δ: 0.01 (3H, s), 0.5 (3H, s), 0.07 (3H, s), 0.11 (3H, s), 0.89 (9H, s), 0.90 (9H, s), 0.90 (3H, d, J=7.0 Hz), 1.78 (1H, dquin, J=4.9, 7.0 Hz), 1.93 (1H, t, J=2.8 Hz), 2.26 (1H, ddd, J=2.8, 7.0, 16.8 Hz), 2.40 (1H, ddd, J=2.8, 4.3, 16.8 Hz), 3.86 (1H, dt, J=7.0, 4.3 Hz), 4.11 (1H, ddt, J=5.8, 7.3, 1.8 Hz), 5.09 (1H, dt, J=10.1, 1.8 Hz), 5.14 (1H, dt, J=17.4, 1.8 Hz), 5.84 (1H, ddd, J=7.3, 10.1, 17.4 Hz).

Reference Example 13

Syntheses of acetonides [determination of the absolute configuration of an ene-yne compound (III)]

Each (5 mg) of the above ene-yne compounds was dissolved in 0.4 ml of acetone, and the resultant solution was allowed to stand at room temperature for 5 hr after the addition of 0.1 ml of dimethoxypropane and CSA (1.5 mg, 0.2 equivalent). The reaction mixture was evaporated, and the obtained crude product was purified by silica gel column chromatography (6 g, 5% AcOEt-hexane>to obtain an acetonide.

Synthesis of a Compound (62) from the Compound (22)

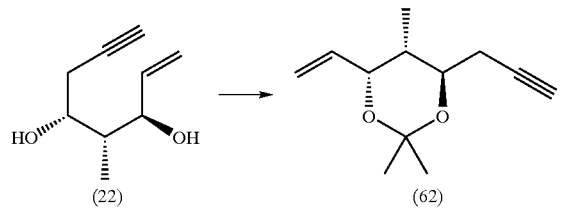

Yield: 80% (colorless oil).

$^1$H-NMR (400 MHz, CDCl$_3$/TMS) δ: 0.90 (3H, d, J=7.0 Hz), 1.39 (3H, s), 1.40 (3H, s), 1.86–1.92 (1H, m), 2.01 (1H, t, J=2.8 Hz), 2.44 (1H, ddd, J=2.8, 6.1, 17.4 Hz), 2.48 (1H, ddd, J=2.8, 5.5, 17.4 Hz), 3.49 (1H, dt, J=7.6, 5.8 Hz), 4.43 (1H, ddt, J=6.1, 5.2, 1.5 Hz), 5.17 (1H, dt, J=10.7, 1.2 Hz), 5.26 (1H, dt, J=17.4, 1.2 Hz), 5.79 (1H, ddd, J=6.1, 10.7, 17.4 Hz)

$^{13}$C-NMR (100 MHz, CDCl$_3$/TMS) δ: 12.89 (q), 24.10 (q), 25.24 (q), 29.70 (t), 39.76 (d), 69.66 (s), 70.61 (d), 73.02 (d), 80.96 (d), 100.88 (s), 115.77 (t), 135.59 (t).

Synthesis of a compound (63) from the compound (23)

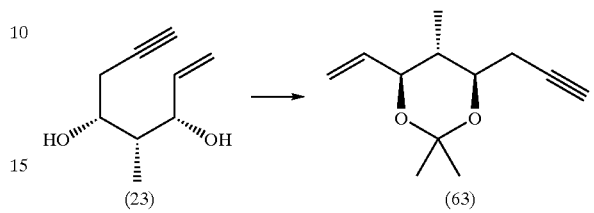

Yield: 80% (colorless oil).

$^1$H-NMR (400 MHz, CDCl$_3$/TMS) δ: 0.82 (3H, d, J=6.7 Hz), 1.45 (3H, s), 1.49 (3H, s), 1.51–1.61 (1H, m), 2.01 (1H, t, J=2.7 Hz), 2.42 (1H, ddd, J=2.7, 5.5, 17.4 Hz), 2.52 (1H, ddd, J=2.7, 4.0, 17.4 Hz), 3.68 (1H, ddd, J=4.0, 5.8, 10.1 Hz), 3.91 (1H, ddt, J=7.3, 10.1, 1.5 Hz), 5.24 (1H, dd, J=1.5, 7.3 Hz), 5.29 (1H, dd, J=1.5, 17.4 Hz), 5.76 (1H, ddd, J=7.3, 10.1, 17.4 Hz).

$^{13}$C-NMR (100 MHz, CDCl$_3$/TMS) δ: 12.15 (q), 19.71 (q), 29.70 (t), 30.04 (q), 39.76 (d), 69.66 (s), 70.61 (d), 73.02 (d), 80.96 (d), 100.88 (s), 115.77 (t), 135.59 (t).

Each of the following ene-yne compounds was synthesized by using an appropriate raw material and applying a similar process.

Reference Example 14 Synthesis of (3S,4R,5R)-3,5-bis(t-butyldimethylsilyloxy)-4-methyl-1-octen-7-yne (39)

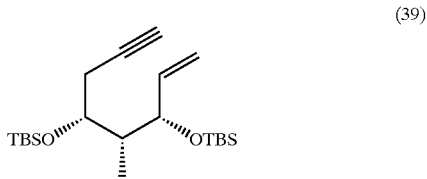

$^1$H-NMR (400 MHz, CDCl$_3$/TMS) δ: 0.02 (3H, s), 0.057 (3H, s), 0.063 (3H, s), 0.11 (3H, s), 0.78 (3H, d, J=7.0 Hz), 0.86 (9H, s), 0.90 (9H, s), 1.89 (1H, dquin, J=5.5, 7.0 Hz), 1.93 (1H, t, J=2.8 Hz), 2.26 (1H, ddd, J=2.8, 7.0, 16.8 Hz), 2.39 (1H, ddd, J=2.8, 4.0, 16.8 Hz), 3.97 (1H, ddd, J=4.0, 5.2, 6.7 Hz), 4.12 (1H, ddt, J=6.4, 6.7, 1.2 Hz), 5.09 (1H, dt, J=10.4, 1.2 Hz), 5.16 (1H; dt, J=17.1, 1.2 Hz), 5.75 (1H, ddd, J=6.1, 10.4, 17.1 Hz).

MS m/z: 382 (M$^+$), 367 (M$^+$-Me), 325 (M$^+$-tBu).

Reference Example 15

Synthesis of (3R,4R, 5S)-3,5-bis(t-butyldimethylsilyloxy)-4-methyl-1-octen-7-yne (40)

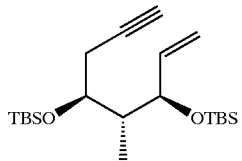

(40)

$^1$H-NMR (400 MHz, CDCl$_3$/TMS) δ: 0.01 (3H, s), 0.049 (3H, s), 0.051 (3H, s), 0.08 (3H, s), 0.89 (18H, s), 0.92 (3H, d, J=7.0 Hz), 1.86 (1H, dquin, J=4.0, 6.7 Hz), 1.95 (1H, t, J=2.8 Hz), 2.38 (2H, dd, J=2.7, 5.8 Hz), 3.88 (1H, ddd, J=4.0, 6.1, 6.4 Hz), 4.09 (1H, t, J=7.0 Hz), 5.10 (1H, dt, J=10.4, 1.5 Hz), 5.14 (1H, dt, J=17.4, 1.5 Hz), 5.81 (1H, ddd, J=7.0, 10.4, 17.4 Hz).

MS m/z: 382 (M$^+$), 367 (M$^+$-Me), 325 (M$^+$-tBu).

Reference Example 16

Synthesis of (3S,4R,5S)-3,5-bis(t-butyldimethylsilyloxy)-4-methyl-1-octen-7-yne (41)

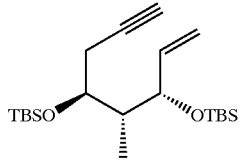

(41)

$^1$H-NMR (400 MHz, CDCl$_3$/TMS) δ: 0.03 (3H, s), 0.06 (3H, s), 0.07 (3H, s), 0.08 (3H, s), 0–76 (3H, d, J=7.0 Hz), 0.889 (9H, s), 0.892 (9H, s), 1.91 (1H, dquin, J=3.7, 7.0 Hz), 1.97 (1H, t, J=2.8 Hz), 2.36–2.40 (2H, m), 3.99–4.05 (2H, m), 5.09 (1H, dt, J=10.4, 0.9 Hz), 5.13 (1H, dt, J=17.1, 0.9 Hz), 5.73 (1H, ddd, J=7.6, 10.1, 17.1 Hz).

MS m/z: 382 (M$^+$), 367 (M$^+$-Me), 325 (M$^+$-tBu).

Reference Example 17

Synthesis of (3R,4S,5R)-3,5-bis(t-butyldimethylsilyloxy)-4-methyl-1-octen-7-yne (42)

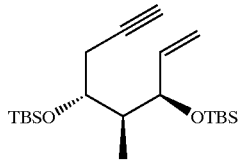

(42)

$^1$H-NMR (400 MHz, CDCl$_3$/TMS) δ: 0.03 (3H, s), 0.06 (3H, s), 0.07 (3H, s), 0.08 (3H, s), 0.76 (3H, d, J=7.0 Hz), 0.889 (9H, s), 0.891 (9H, s), 1.91 (1H, dquin, J=3.7; 7.0 Hz), 1.97 (1H, t, J=2.8 Hz), 2.31–2.43 (2H, m), 3.98–4.04 (2H, m), 5.10 (1H, dt, J=10.1, 1.5 Hz), 5.13 (1H, dt, J=17.1, 1.5 Hz), 5.74 (1H, ddd, J=7.6, 10.1, 17.1 Hz).

MS m/z: 382 (M$^+$), 367 (M$^+$-Me), 325 (M$^+$-tBu).

Reference Example 18

Synthesis of (3S,4S,5R)-3,5-bis(t-butyldimethylsilyloxy)-4-methyl-1-octen-7-yne (43)

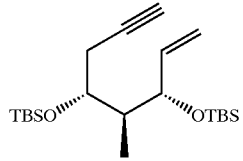

(43)

$^1$H-NMR (400 MHz, CDCl$_3$/TMS) δ: 0.01 (3H, s), 0.049 (3H, s), 0.051 (3H, s), 0.08 (3H, s), 0.89 (18H, s), 0.92 (3H, d, J=7.0 Hz), 1.85 (1H, dquin, J=3.7, 6.7 Hz), 1.96 (1H, t, J=2.8 Hz), 2.39 (2H, dd, J=2.8, 6.7 Hz), 3.88 (1H, ddd, J=4.0, 6.1, 6.4 Hz), 4.07 (1H, t, J=6.7 Hz), 5.10 (1H, dt, J=10.1, 1.8 Hz), 5.14 (1H, dt, J=18.3, 1.8 Hz), 5.81 (1H, ddd, J=7.0, 10.4, 17.4 Hz).

MS m/z: 367 (M$^+$-Me), 325 (M$^+$-tBu).

Reference Example 19

Synthesis of (3R,4S,5S)-3,5-bis(t-butyldimethylsilyloxy)-4-methyl-1-octen-7-yne (44)

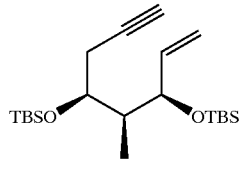

(44)

$^1$H-NMR (400 MHz, CDCl$_3$/TMS) δ: 0.01 (3H, s), 0.057 (3H, s), 0.063 (3H, s), 0.11 (3H, s), 0.78 (3H, d, J=7.0 Hz), 0.86 (9H, s), 0.90 (9H, s), 1.88 (1H, dquin, J=5.5, 6.7 Hz), 1.93 (1H, t, J=2.8 Hz), 2.26 (1H, ddd, J=2.8, 7.0, 16.8 Hz), 2.39 (1H, ddd, J=2.8, 4.0, 16.8 Hz), 3.97 (1H, dt, J=4.0, 5.5 Hz), 4.12 (1H, ddt, J=5.2, 6.7, 1.2 Hz), 5.09 (1H, dt, J=10.4, 1.2 Hz), 5.15 (1H, dt, J=17.1, 1.2 Hz), 5.75 (1H, ddd, J=6.7, 10.4, 17.4 Hz).

MS m/z: 382 (M$^+$), 367 (M$^+$-Me), 325 (M$^+$-tBu).

Reference Example 20

Synthesis of (3S,4S,5S)-3,5-bis(t-butyldimethylsilyloxy)-4-methyl-1-octen-7-yne (45)

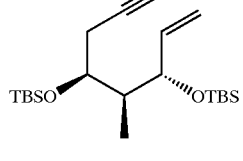

(45)

$^1$H-NMR (400 MHz, CDCl$_3$/TMS) δ: 0.01 (3H, s), 0.05 (3H, s), 0.07 (3H, s), 0.10 (3H, s), 0.88 (3H, d, J=7.0 Hz), 0.89 (9H, s), 0.90 (9H, s), 1.76–1.80 (1H, m), 1.93 (1H, t, J=2.8 Hz), 2.26 (1H, ddd, J=2.7, 7.0, 16.8 Hz), 2.40 (1H, ddd, J=2.7, 4.3, 16.8 Hz), 3.85 (1H, dt, J=7.0, 4.3 Hz), 4.11 (1H, ddt, J=5.8, 7.3, 1.8 Hz), 5.10 (1H, dt, J=10.1, 1.8 Hz), 5.14 (1H, dt, J=17.4, 1.8 Hz), 5.84 (1H, ddd, J=7.3, 10.1, 17.4 Hz).

MS m/z: 382 (M$^+$), 367 (M$^+$-Me), 325 (M$^+$-tBu).

Example 1

Synthesis of (20S)-1α,25-dihydroxy-2α-methyl-3β-vitamin $D_3$ (72)

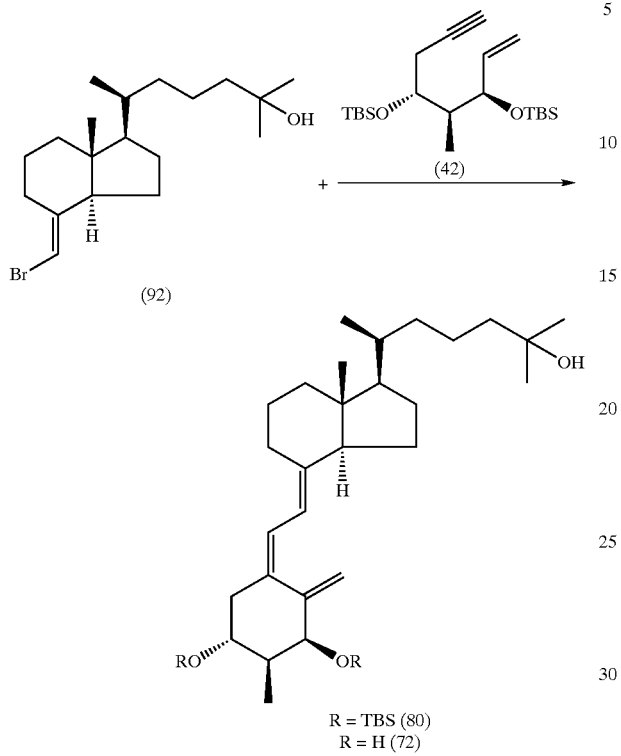

R = TBS (80)
R = H (72)

An exo-methylene compound (92) (17 mg) was dissolved in 0.3 ml of toluene, and $Et_3N$ (0.45 ml) was added to the resultant solution under argon atmosphere. $Pd_2(dba)_3 \cdot CHCl_3$ (1.9 mg, 0.03 equivalent) and $Ph_3P$ (2.5 mg, 0.3 equivalent) were added, the resultant mixture was stirred at room temperature, then a toluene solution (0.2 ml) of the ene-yne compound (42)(13 mg, 0.7 equivalent) was added, and the mixture was stirred at room temperature for 10 min, and further made to react on an oil bath of 120° C. for 2.5 hr. After cooling, the reaction mixture was filtered, and the filtrate was purified by silica gel chromatography (AcOEt:hexane=1:3) to obtain a compound (80).

The obtained compound (80) was dissolved in 1 ml of methanol, CSA (11 mg, 1 equivalent) was added to the resultant solution, the mixture was made to react overnight at room temperature under argon atmosphere. The reaction mixture was evaporated, the residue was extracted with AcOEt after the addition of purified water. The extract was washed with brine, dried over magnesium sulfate and evaporated. The obtained crude product was purified by silica gel chromatography (AcOEt:hexane=1:1) and further by recycle-preparative HPLC (Lichrosorb RP-18, 70% MeCN/$H_2O$) to obtain colorless crystal (72) (9.3 mg, 6.3%).

$^1$H-NMR (400 MHz, $CDCl_3$-$D_2O$/TMS) δ: 0.53 (3H, s), 0.85 (3H, d, J=6.7 Hz), 1.08 (3H, d, J=6.8 Hz), 1.21 (6H, s), 1.12–2.04, (19H, m) 2.23 (1H, dd, J=7.9, 13.4 Hz), 2.67 (1H, dd, J=4.0, 13.4 Hz), 2.83 (1H, m), 3.83 (1H, td, J=7.9, 4.0 Hz), 4.29 (1H, d, J=3.3 Hz), 5.01 (1H, d, J=1.8 Hz), 5.28 (1H, m), 6.01 (1H, d, J=11.3 Hz), 6.39 (1H, d, J=11.3 Hz).

UV (EtOH). λ max: 266 nm.

MS m/z: 430 ($M^+$), 412 ($M^+$-$H_2O$), 394 ($M^+$-$2H_2O$).

HR-MS, calculated for $C_{28}H_{46}O_3$: 430.3447, found: 430.3443.

Using reaction conditions similar to Example 1, the following 1,25-dihydroxy-2-methylvitamin $D_3$ derivatives were prepared.

Example 2

Synthesis of (20S)-α,25-dihydroxy-2β-methyl-3β-vitamin $D_3$ (68)

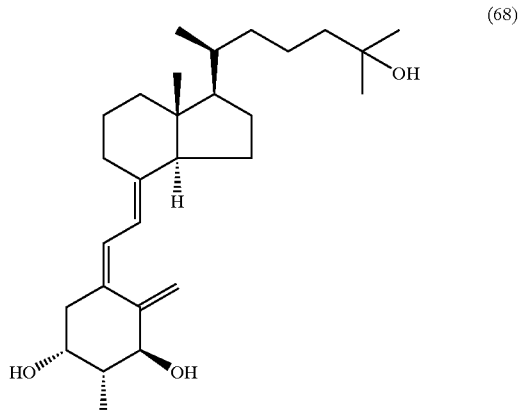

$^1$H-NMR (400 MHz, $CDCl_3$-$D_2O$/TMS) δ: 0.55 (3H, s), 0.85 (3H, d, J=6.4 Hz), 1.15 (3H, d, J=6.7 Hz), 1.21 (6H, s), 1.17–2.01, (19H, m) 2.42 (1H, dd, J=13.9, 4.9 Hz), 2.52 (1H, d, J=13.9 Hz), 2.82 (1H, dd, J=11.9, 4.0 Hz), 3.99–4.04 (1H+1H, m), 5.02 (1H, t, J=1.8 Hz), 5.37 (1H, t, J=1.8 Hz), 6.03 (1H, d, J=11.3 Hz), 6.35 (1H, d, J=11.3 Hz).

UV(EtOH) λ max: 263 nm.

MS m/z: 430 ($M^+$), 412 ($M^+$-$H_2O$), 394 ($M^+$-$2H_2O$).

HR-MS, calculated for $C_{28}H_{46}O_3$: 430.3447, found: 430.3441.

Example 3

Synthesis of (20S)-1β,25-dihydroxy-2β-methyl-3β-vitamin $D_3$ (69)

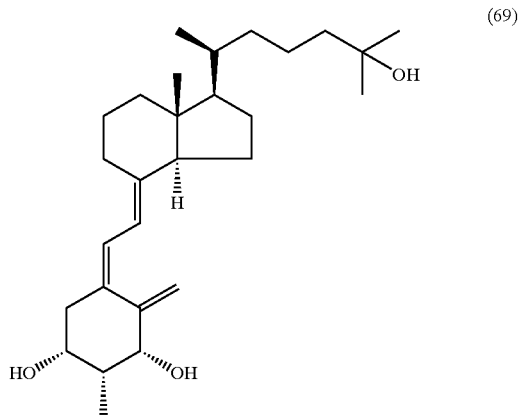

$^1$H-NMR (400 MHz, $CDCl_3$/TMS) δ: 0.55 (3H, s), 0.85 (3H, d, J=6.7 Hz), 1.22 (6H, s), 1.23 (3H, d, J=7.3 Hz), 2.17 (1H, d, J=4.3 Hz), 2.50 (1H, brd, J=12.5 Hz), 2.59(1H, dd, J=14.0, 3.7 Hz), 2.79 (1H, d, J=7.6 Hz), 2.85 (1H, dd, J=12.5, 4.9 Hz), 3.91(1H, m), 4.17 (1H, m), 5.01 (1H, d, J=2.1 Hz), 5.25 (1H, d, J=1.8 Hz), 6.09 (1H, d, J=11.3 Hz), 6.48 (1H, d, J=11.3 Hz).

MS m/z: 430 (M⁺), 412 (M⁺-H₂O), 394 (M⁺-2H₂O), 379 (M⁺-2H₂O-Me).

HR-MS, calculated for $C_{28}H_{46}O_3$: 430.3447, found: 430.3446.

Example 4

Synthesis of (20S)-1α,25-dihydroxy-2β-methyl-3α-vitamin D₃ (70)

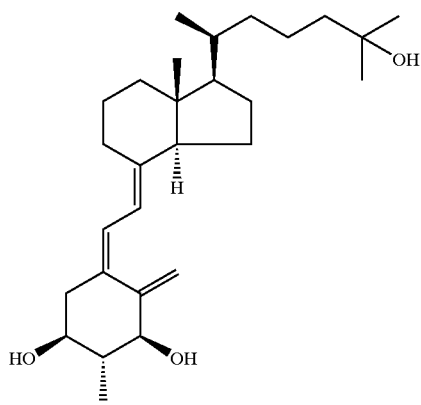

(70)

¹H-NMR (400 MHz, CDCl₃/TMS) δ: 0.54 (3H, s), 0.85 (3H, d, J=6.4 Hz), 1.06 (3H, d, J=7.0 Hz), 1.22 (6H, s), 2.12 (1H, d, J=2.8 Hz), 2.34 (1H, dd, J=14.7, 7.0 Hz), 2.60 (1H, brs), 2.64 (1H, dd, J=13.4, 2.8 Hz), 2.84 (1H, dd, J=11.6, 3.1 Hz), 3.65 (1H, m), 3.90(1H, m), 5.05 (1H, d, J=1.8 Hz), 5.30 (1H, d, J=2.7 Hz), 6.02 (1H, d, J=11.3 Hz), 6.41 (1H, d, J=11.3 Hz).

MS m/z: 430 (M⁺), 412 (M⁺-H₂O), 394 (M⁺-2H₂O), 379 (M⁺-2H₂O-Me).

HR-MS, calculated for $C_{28}H_{40}O_3$: 430.3447, found: 430.3447.

Example 5

Synthesis of (20S)-1β,25-dihydroxy-2β-methyl-3α-vitamin D₃ (71)

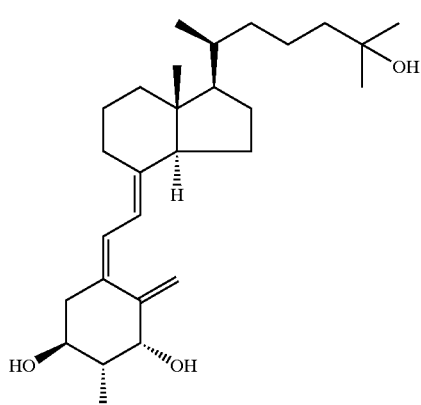

(71)

¹H-NMR (400 MHz, CDCl₃/TMS) δ: 0.54 (3H, s), 0.85 (3H, d, J=6.4 Hz), 1.10 (3H, d, J=6.7 Hz), 1.22 (6H, s), 1.68 (2H, m), 1.85 (2H, m), 1.98 (2H, m), 2.24 (1H, dd, J=13.4, 8.5 Hz), 2.65 (1H, dd, J=13.4, 4.3 Hz), 2.82 (1H, dd, J=12.2, 4.3 Hz), 3.81 (1H, m>, 4.27 (1H, m), 5.02 (1H, d, J=2.1 Hz), 5.28 (1H, d, J=1.8 Hz), 6.02 (1H, d, J=11.3 Hz), 6.40 (1H, d, J=11.3 Hz).

MS m/z: 430 (M⁺), 412 (M⁺-H₂O), 394 (M⁺-2H₂O), 379 (M⁺-2H₂O-Me).

HR-MS, calculated for $C_{28}H_{46}O_3$: 430.3447, found: 430.3446.

Example 6

Synthesis of (20S)-1β,25-dihydroxy-2α-methyl-3β-vitamin D₃ (73)

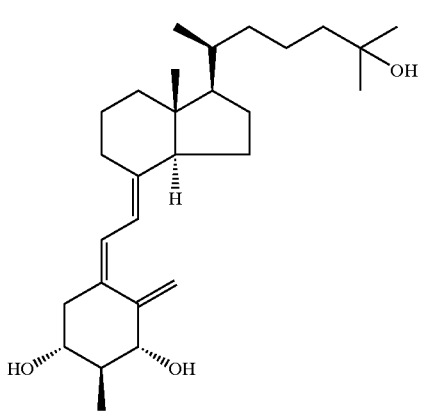

(73)

¹H-NMR (400 MHz, CDCl₃/TMS) δ: 0.55 (3H, s), 0.85 (3H, d, J=6.4 Hz), 1.02 (3H, d, J=7.0 Hz), 1.22 (6H, s), 1.83 (1H, m), 2.00 (2H, m), 2.11 (1H, m), 2.27 (1H, d, J=7.0 Hz), 2.34 (1H, dd, J=14.0, 5.5 Hz), 2.65 (1H, dd, J=14.0, 7.8 Hz), 2.84 (1H, dd, J=12.2, 4.3 Hz), 3.72 (1H, m), 3.97 (1H, t, J=4.9 Hz), 5.07 (1H, d, J=2.1 Hz), 5.30 (1H, d, J=2.1 Hz), 6.04 (1H, d, J=11.3 Hz), 6.43 (1H, d, J=11.3 Hz).

MS m/z: 430 (M⁺), 412 (M⁺-H₂O), 394 (M⁺-2H₂O), 379 (M⁺-2H₂O-Me).

HR-MS, calculated for $C_{28}H_{46}O_3$: 430.3447, found: 430.3445.

Example 7

Synthesis of (20S)-1α,25-dihydroxy-2 α-methyl-3α-vitamin D₃ (74)

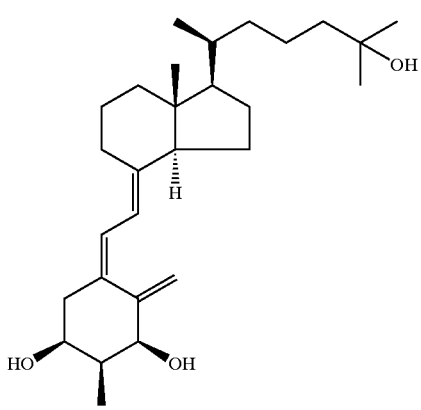

(74)

¹H-NMR (400 MHz, CDCl₃/TMS) δ: 0.53 (3H, s), 0.85 (3H, d, J=6.4 Hz), 1.21 (6H, s), 1.22 (3H, d, J=7.0 Hz), 2.09 (1H, d, J=4.6 Hz), 2.49 (1H, d, J=14.7 Hz), 2.58 (1H, dd, J=14.0, 3.7 Hz), 2.80 (1H, d, J=7.9 Hz), 2.85 (1H, m), 3.91 (1H, m), 4.17 (1H, m), 4.98 (1H, d, J=2.1 Hz), 5.23 (1H, d, J=1.8 Hz), 6.03 (1H, d, J=11.3 Hz), 6.48 (H, d, J=11.3 Hz).

MS m/z: 430 (M$^+$), 412 (M$^+$-H$_2$O), 394 (M$^+$-2H$_2$O), 379 (M$^+$-2H$_2$O-Me).

HR-MS, calculated for C$_{28}$H$_{46}$O$_3$: 430.3447, found: 430.3447.

Example 8

Synthesis of (20S)-1β,25-dihydroxy-2α-methyl-3α-vitamin D$_3$ (75)

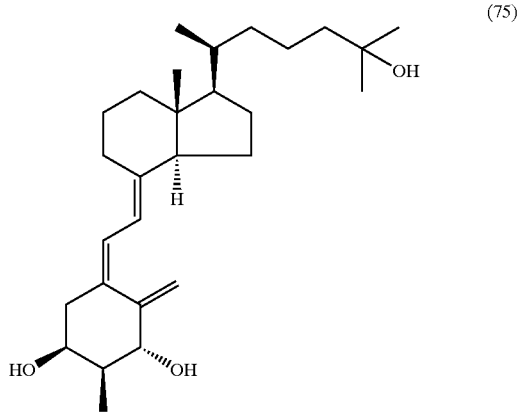

$^1$H-NMR (400 MHz, CDCl$_3$/TMS) δ: 0.53 (3H, s), 0.85 (3H, d, J=6.4 Hz), 1.13 m (3H, d, J=6.7 Hz), 1.21 (6H, s), 1.69 (2H, m), 1.84 (2H, m), 1.98 (2H, m), 2.41 (1H, dd, J=13.7, 5.5 Hz), 2.51 (1H, dd, J=13.4, 2.4 Hz), 2.82 (1H, m), 4.02–4.08 (2H, m), 5.01 (1H, d, J=1.8 Hz), 5.35 (1H, d, J=1.8 Hz), 6.01 (1H, d, J=11.6 Hz), 6.36 (1H, d, J=11.6 Hz).

MS m/z: 430 (M$^+$), 412 (M$^+$-H$_2$O), 394 (M$^+$-2H$_2$O), 379 (M$^+$-2H$_2$O-Me).

HR-MS, calculated for C$_{28}$H$_{46}$O$_3$: 430.3447, found: 430.3445.

Example 9

Binding Affinities of Objective Compounds of the Present Invention for a Bovine Thymus 1α,25-dihydroxyvitamin D$_3$ receptor (VDR)

The content (about 25 mg) of an ampule of a bovine thymus vitamin D receptor kit made by Yamasa Shoyu Ltd. was dissolved in 55 ml of a 0.05 M phosphoric acid-0.5 M potassium buffer solution (pH 7.4). Fifty μl of the ethanol solution of a compound to be tested and 500 μl of the receptor solution were pre-incubated at room temperature for 1 hr. To the treated mixture, 50 μl of a [26,27-methyl-$^3$H]1α,25-dihydroxyvitamin D$_3$ solution (131 Ci/mmol, 16,000 dpm) was added so that the final concentration became 0.1 nM, and the resultant mixture was incubated overnight at 4° C. Both of the bound and the non-bound [26,27-methyl-$^3$H]1α,25-dihydroxy-vitamins D$_3$ were subjected to centrifugation after the addition of 200 μl of dextran-coated charcoal. To 500 μl of the supernatant, 9.5 ml of a liquid scintillation cocktail (ACS-II) was added, and the radioactivity of the resultant mixture was measured by a liquid scintillation counter.

The binding affinity of a compound to be tested for the D$_3$-receptor (VDR) was expressed by a relative intensity ratio based on 100 for 1α,25-dihydroxyvitamin D$_3$ by determining the concentration which inhibits the binding of [26,27-methyl-$^3$H]1α,25-dihydroxy-vitamin D$_3$ by 50%. The results are shown in the following Table.

| Compound | Binding Affinity for VDR | Compound | Binding Affinity for VDR |
|---|---|---|---|
| 1α,25-(OH)$_2$VD$_3$ | 100 | Compound (68) | 160 |
| Compound (65) | 13 | Compound (69) | 0.03 |
| Compound (1) | 0.05 | Compound (70) | 0.08 |
| Compound (2) | 0.3 | Compound (71) | 7 |
| Compound (3) | 0.8 | Compound (72) | 1200 |
| Compound (4) | 400 | Compound (73) | 0.05 |
| Compound (5) | 0.05 | Compound (74) | 17 |
| Compound (6) | 4 | Compound (75) | 0.03 |
| Compound (7) | 0.06 | | |

Herein, the compounds (1) to (7) and the compound (65) shown in the above table are reference examples, and are expressed by the followings, respectively.
(20R)-1β,25-dihydroxy-2β-methyl-3β vitamin D$_3$,
(20R)-1α,25-dihydroxy-2β-methyl-3α vitamin D$_3$,
(20R)-1β,25-dihydroxy-2β-methyl-3β vitamin D$_3$,
(20R)-1α,25-dihydroxy-2α-methyl-3β vitamin D$_3$,
(20R)-1β,25-dihydroxy-2α-methyl-3β vitamin D$_3$,
(20R)-1β,25-dihydroxy-2α-methyl-3β vitamin D$_3$,
(20R)-1α,25-dihydroxy-2α-methyl-3α vitamin D$_3$,
(20R)-1β,25-dihydroxy-2α-methyl-3α vitamin D$_3$ and
(20R)-1α,25-dihydroxy-2β-methyl-3β vitamin D$_3$.

Example 10

Activities of Objective Compounds of the Present Invention on Differentiation Induction effect of HL-60 Cell HL-60 cell was purchased from a cell bank (Japanese Cancer Research Resource Bank, Cell Number: JCRB 0085). The cell was stored as a frozen storage stock for preventing the change of cell characteristics attributable to successive cultivation. Before the initiation of experiments, the cell was defrosted, and successive cultivation was started for using the cell in the experiments. The cell which had been treated by successive culturing for about one to six months was used for the experiments. The successive culturing was carried out by centrifugally recovering cells from cultivation mixture in suspension culture, and diluting the collected cell concentrate in a fresh culture medium at a ratio of about 1/100 (1–2×10$^5$ cells/ml). As the culture medium, an RPMI-1640 medium containing 10% fetal bovine serum was used. Successively cultured cells were centrifugally collected, and they were dispersed in a culture medium at the concentration of 2×10$^4$ cells/ml. The dispersion was seeded into a 24-well culture petri dish at 1 ml/well. An ethanol solution (1×10$^{-9}$M to 1×10$^{-6}$M) of a compound of the present invention was added to this system at 1 μl/well. Further, regarding 1 α,25(OH)$_2$D$_3$, an ethanol solution of 1×10$^{-7}$ M to 1×10$^{-4}$ M was added at 1 μl/well, and for the control, ethanol was added at 1 μl/well. After culturing at 37° C. for 4 days under a 5% CO$_2$ atmosphere, the cells were centrifugally collected. Nitroblue tetrazolium (NBT) reduction activity was determined as follows. That is, the collected cells were suspended in a fresh culture medium, and NBT and 12-O-tetradecanoylphorbol-13-acetate were added to the resultant suspension so that their concentrations became 0.1% and 100 nM, respectively. After the mixed suspension was incubated at 37° C. for 25 min, a cytospin sample was prepared. After air drying, it was stained with Kernechtrot, and the ratio of the positive cells of NBT reduction activity was determined under an optical microscope. The results are shown in the following Table.

Activities of Compounds of the Present Invention on Nitroblue Tetrazolium

| Compound | Concentration (M) | Positive cells (%) of nitroblue tetrazolium reduction activity |
|---|---|---|
| Control | | 1.5 |
| $1\alpha,25$-$(OH)_2D_3$ | $10^{-10}$ | 4.3 ± 1.2 |
| | $10^{-9}$ | 36.8 ± 2.0 |
| | $10^{-8}$ | 86.1 ± 2.6 |
| | $10^{-7}$ | 96.5 ± 1.0 |
| Compound (68) | $10^{-12}$ | 1.7 ± 0.3 |
| | $10^{-11}$ | 2.8 ± 0.7 |
| | $10^{-10}$ | 57.7 ± 5.0 |
| | $10^{-9}$ | 95.7 ± 1.0 |
| Compound (71) | $10^{-12}$ | 1.5 ± 0.8 |
| | $10^{-11}$ | 1.8 ± 0.8 |
| | $10^{-10}$ | 2.0 ± 1.0 |
| | $10^{-9}$ | 40.5 ± 1.8 |
| Compound (74) | $10^{-12}$ | 6.4 ± 1.1 |
| | $10^{-11}$ | 17.0 ± 2.3 |
| | $10^{-10}$ | 16.7 ± 1.1 |
| | $10^{-9}$ | 96.4 ± 1.4 |
| Compound (72) | $10^{-12}$ | 3.7 ± 0.8 |
| | $10^{-11}$ | 94.4 ± 1.8 |
| | $10^{-10}$ | 95.7 ± 2.3 |
| | $10^{-9}$ | 96.2 ± 2.0 |

Industrial Field of Application

Each of 1,25-dihydroxy-2-methylvitamin $D_3$ derivatives expressed the above formula (I) provided by the present invention can be effectively used for diseases (osteoporosis, rickets, hyperthyroidism, etc.) for which the usefulness of vitamin $D_3$ derivatives are widely recognized. Among these diseases, compounds of the present invention are especially effective for diseases (tumors, psoriasis, etc.) attributable to cell differentiation failure owing to extremely strong differentiation-inducing activity.

Further, each of 1,25-dihydroxy-2-methylvitamin $D_3$ derivatives exhibits different affinities for between a vitamin D receptor and a vitamin D binding protein depending on the kind of stereoisomer derived from the 1-, 2- and 3-positions, in such a manner that a stereoisomer has high affinity for the vitamin D receptor and at the same time high affinity for the vitamin D binding protein, and another isomer has a high affinity for the vitamin D receptor but a low affinity for the vitamin D binding protein. The derivatives therefore are useful as treating agents for vitamin D metabolic disorders suitably corresponding to characteristics of action of the derivatives.

What is claimed is:

1. A 1,25-dihydroxy-2-methylvitamin $D_3$ compound, wherein the compound is
(i) (20S)-$1\alpha$,25-dihydroxy-$2\beta$-methyl-$3\beta$-vitamin $D_3$;
(ii) (20S)-$1\beta$,25-dihydroxy-$2\beta$-methyl-$3\alpha$-vitamin $D_3$;
(iii) (20S)-$1\alpha$,25-dihydroxy-$2\alpha$-methyl-$3\beta$-vitamin $D_3$; or
(iv) (20S)-$1\alpha$,25-dihydroxy-$2\alpha$-methyl-$3\alpha$-vitamin $D_3$.

2. A method for producing a vitamin $D_3$ compound described in claim 1, comprising reacting an exo-methylene compound of formula (II):

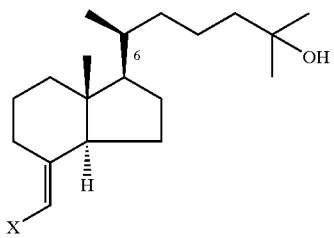

wherein X is a bromine atom or an iodine atom, with an eneyne compound of formula (III):

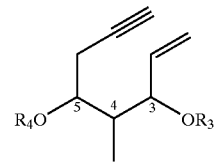

wherein $R_3$ and $R_4$ are each independently a hydrogen atom or a tri($C_1$ to $C_7$ hydrocarbon)silyl group in the presence of a palladium catalyst, and optionally removing the protecting group of the tri($C_1$ to $C_7$ hydrocarbon)silyl group, and further wherein the vitamin $D_3$ compound is
(i) (20S)-$1\alpha$,25-dihydroxy-$2\beta$-methyl-$3\beta$-vitamin $D_3$;
(ii) (20S)-$1\beta$,25-dihydroxy-$2\beta$-methyl-$3\alpha$-vitamin $D_3$;
(iii) (20S)-$1\alpha$,25-dihydroxy-$2\alpha$-methyl-$3\beta$-vitamin $D_3$; or
(iv) (20S)-$1\alpha$,25-dihydroxy-$2\alpha$-methyl-$3\alpha$-vitamin $D_3$.

* * * * *